US011618780B2

(12) United States Patent
Morris et al.

(10) Patent No.: US 11,618,780 B2
(45) Date of Patent: Apr. 4, 2023

(54) COMPOSITION AND METHOD FOR ACTIVATING LATENT HUMAN IMMUNODEFICIENCY VIRUS (HIV)

(71) Applicant: City of Hope, Duarte, CA (US)

(72) Inventors: Kevin V. Morris, Sierra Madre, CA (US); Marc S. Weinberg, Encinitas, CA (US); Tristan Scott, Pasadena, CA (US); Daniel Lazar, San Diego, CA (US)

(73) Assignee: CITY OF HOPE, Duarte, CA (US)

( * ) Notice: Subject to any disclaimer, the term of this patent is extended or adjusted under 35 U.S.C. 154(b) by 338 days.

(21) Appl. No.: 16/756,632

(22) PCT Filed: Oct. 22, 2018

(86) PCT No.: PCT/US2018/056943
§ 371 (c)(1),
(2) Date: Apr. 16, 2020

(87) PCT Pub. No.: WO2019/079819
PCT Pub. Date: Apr. 25, 2019

(65) Prior Publication Data
US 2020/0255500 A1 Aug. 13, 2020

Related U.S. Application Data

(60) Provisional application No. 62/575,307, filed on Oct. 20, 2017.

(51) Int. Cl.
*C07K 14/00* (2006.01)
*C07K 16/10* (2006.01)

(52) U.S. Cl.
CPC .............. *C07K 16/10* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,334,575 A | 8/1994 | Noonan et al. | |
| 5,403,841 A | 4/1995 | Lang et al. | |
| 5,888,795 A | 3/1999 | Hamilton | |
| 2004/0039175 A1 | 2/2004 | Choo et al. | |
| 2011/0263460 A1 | 10/2011 | Quinones-Mateu et al. | |
| 2015/0173367 A1* | 6/2015 | Sera ................... | C12N 15/8283 800/301 |
| 2016/0017301 A1 | 1/2016 | Khalili et al. | |

OTHER PUBLICATIONS

Al-Muhammed, J. et al. (May-Jun. 1996). "In-vivo studies on dexamethasone sodium phosphate liposomes," *J Microencapsul* 13(3):293-306.

Altschul, S.F. et al. (Oct. 5, 1990). "Basic local alignment search tool," *J Mol Biol* 215(3):403-410.
Altschul, S.F. et al. (Sep. 1, 1997). "Gapped BLAST and PSI-BLAST: a new generation of protein database search programs," *Nucleic Acids Research* 25(17):3389-3402.
Bailus B.J. et al. (Mar. 2016, e-published Jan. 4, 2016). "Protein Delivery of an Artificial Transcription Factor Restores Widespread Ube3a Expression in an Angelman Syndrome Mouse Brain," *Mol Ther*. 24(3):548-555.
Benjamin, R. et al. (Aug. 21, 2014). "Mycobacterial and HIV Infections Up-Regulated Human Zinc Finger Protein 134, a Novel Positive Regulator of HIV-1 LTR Activity and Viral Propagation," *PLoS One* 9(8):e104908.
Clarke, A.R. (Dec. 1993). "Transgenic Approaches to Cancer Biology," *Curr Opin Biotechnol* 4(6):699-704.
Chonn, A. et al. (Dec. 1995). "Recent advances in liposomal drug-delivery systems," *Curr Opin Biotechnol* 6(6):698-708.
Eyles, J.E. et al. (Jul. 1997). "Oral delivery and fate of poly(lactic acid) microsphere-encapsulated interferon in rats," *J. Pharm. Pharmacol.* 49(7):669-674.
Ford, K.G. et al. (Jan. 2001). "Protein Transduction: An Alternative to Genetic Intervention?" *Gene Ther* 8(1):1-4.
Gao, Z.H. et al. (Jun. 1995). "Controlled release of a contraceptive steroid from biodegradable and injectable gel formulations: in vitro evaluation," *Pharm. Res* 12(6):857-863.
Henikoff, S. et al. (Nov. 15, 1989). "Amino acid substitution matrices from protein blocks," *Proc. Natl. Acad. Sci. USA* 89(22):10915-10919.
International Search Report dated Jan. 18, 2019, for PCT Application No. PCT/US2018/056943, filed Oct. 22, 2018, 5 pages.
Jeeninga, R.E. et. al. (Apr. 2000). "Functional Differences Between the Long Terminal Repeat Transcriptional Promoters of Human Immunodeficiency Virus Type 1 Subtypes A Through G," *J Virol* 74(8):3740-3751.
Karlin, S. et al. (Jun. 15, 1993). "Applications and Statistics for Multiple High-Scoring Segments in Molecular Sequences," *PNAS USA* 90(12):5873-5877.
Klaver, B. et al. (Jun. 1994). "Comparison of 5' and 3' Long Terminal Repeat Promoter Function in Human Immunodeficiency Virus," *J Virol* 68(6):3830-3840.
Needleman, S.B. et al. (Mar. 1970). "A general method applicable to the search for similarities in the amino acid sequence of two proteins," *J Mol Biol* 48(3):443-453.

(Continued)

*Primary Examiner* — Nicole Kinsey White
(74) *Attorney, Agent, or Firm* — Mintz Levin Cohn Ferris Glovsky and Popeo, P.C.

(57) ABSTRACT

Provided are compositions and methods for activating latent Human Immunodeficiency Virus (HIV). The compositions and methods may utilize a recombinant peptide that has a DNA binding zinc finger domain specific to the HIV long terminal repeat (LTR) sequence. The recombinant peptide may also have a transcription factor (e.g. a transcription activator) that is conjugated to the zinc finger domain. Also provided are methods of treating HIV in a subject in need of the treatment. The method may involve activation of latent HIV in cells of the subject and selectively removing such cells from the subject, providing complete and effective treatment of HIV.

12 Claims, 11 Drawing Sheets
Specification includes a Sequence Listing.

(56) References Cited

OTHER PUBLICATIONS

Nishitsuji, H. et al. (Jul. 8, 2015, e-published Jun. 19, 2015). "ZNF10 Inhibits HIV-1 LTR Activity Through Interaction With NF-κB and Sp1 Binding Motifs," *FEBS Lett* 589(15):2019-2025.

Ostro, M.J. et al. (Aug. 1989). "Use of liposomes as injectable-drug delivery systems," *Am J Hosp Pharm* 46(8):1576-1587.

Palva, I. et al. (May-Jun. 1983). "Secretion of Interferon by Bacillus Subtilis," *Gene* 22(2-3):229-235.

Pearson, W.R. et al. (Apr. 1988). "Improved tools for biological sequence comparison," *Proc. Nat'l. Acad. Sci. USA* 85(8):2444-2448.

Prochiantz, A. (Feb. 2007). "For Protein Transduction, Chemistry Can Win Over Biology," *Nat Methods* 4(2):119-120.

Rao. K.P. (1995). "Recent developments of collagen-based materials for medical applications and drug delivery systems," *J. Biomater Sci. Polym. Ed.* 7(7):623-645.

Saayman, S.M. et al. (Mar. 2016, e-published Nov. 19, 2015). "Potent and Targeted Activation of Latent HIV-1 Using the CRISPR/dCas9 Activator Comple," *Mol Ther*.24(3):488-498.

Sakkhachornphop, S. et al. (Nov. 2009). "Designed Zinc Finger Protein Interacting With the HIV-1 Integrase Recognition Sequence at 2-LTR-circle Junctions," *Protein Sci* 18(11):2219-2230.

Smith, T.F. et al. (1981). "Comparison of Biosequences," *Adv. Appl. Math* 2:482-489.

Wang, P. et al. (May 2014, e-published Mar. 13, 2014). "Specific Reactivation of Latent HIV-1 With Designer Zinc-Finger Transcription Factors Targeting the HIV-1 5'-LTR Promoter," *Gen Ther* 21(5):490-495.

Written Opinion dated Jan. 18, 2019, for PCT Application No. PCT/US2018/056943, filed Oct. 22, 2018, 5 pages.

\* cited by examiner

| Gene (chromosome) | start | end | width | Input1 | Input2 | Input3 | myc1 | myc2 | myc3 | mean-fold-zip | annotation |
|---|---|---|---|---|---|---|---|---|---|---|---|
| GAK (chr4) | 908148 | 908658 | 511 | 0.0 | 0.0 | 4.4 | 13.0 | 7.2 | 8.8 | 8.76 | Promoter (2-3kb) |
| ATP6V0A4 (chr7) | 138786677 | 138787102 | 426 | 5.5 | 4.4 | 8.0 | 53.9 | 28.0 | 39.1 | 5.24 | Promoter (2-3kb) |
| chr22 | 23412065 | 23412416 | 352 | 7.5 | 1.1 | 4.6 | 17.8 | 18.4 | 20.4 | 4.38 | Promoter (<1kb) |
| FAM173A (chr4) | 83482742 | 83483120 | 379 | 1.5 | 4.3 | 4.6 | 23.7 | 8.1 | 12.1 | 4.00 | Promoter (<1kb) |
| DKFZP434C062 (chr9) | 138325007 | 138325498 | 492 | 8.4 | 12.2 | 2.8 | 18.3 | 18.6 | 37.2 | 3.94 | Promoter (<1kb) |
| GLTSCR2-AS1 (chr19) | 47780294 | 47780718 | 425 | 2.5 | 9.5 | 3.9 | 25.4 | 12.7 | 25.5 | 3.83 | Promoter (<1kb) |
| KIAA0513 (chr16) | 85044876 | 85045458 | 583 | 3.5 | 4.0 | 5.1 | 20.4 | 12.1 | 29.6 | 3.58 | Promoter (<1kb) |
| TCF7L1 (chr2) | 85133349 | 85133787 | 439 | 4.2 | 6.3 | 6.1 | 14.3 | 19.9 | 39.3 | 3.30 | Promoter (<1kb) |
| SHPM1 (chr7) | 86634609 | 86635092 | 484 | 8.6 | 9.3 | 4.3 | 27.0 | 16.4 | 35.3 | 3.30 | Promoter (<1kb) |
| PRKCE (chr2) | 27603854 | 27606250 | 397 | 8.6 | 11.4 | 5.6 | 30.3 | 26.1 | 32.1 | 3.22 | Promoter (<1kb) |

FIG. 6

| Gene (chromosome) | start | end | width | Input1 | Input2 | Input3 | myc1 | myc2 | myc3 | mean-fold-zip | annotation |
|---|---|---|---|---|---|---|---|---|---|---|---|
| GAK (chr4) | 908348 | 908858 | 511 | 0.0 | 1.3 | 2.0 | 24.3 | 22.6 | 7.3 | 15.70 | Promoter (2-3kb) |
| AHRR (chr5) | 321655 | 322046 | 392 | 3.7 | 4.3 | 0.4 | 18.2 | 14.4 | 7.2 | 5.37 | Promoter (<=1kb) |
| D2P1L (chr0) | 138067210 | 138067509 | 300 | 5.9 | 4.3 | 0.7 | 12.1 | 20.7 | 9.5 | 4.84 | Promoter (<=1kb) |
| TFAP2A (chr6) | 10419086 | 10419397 | 312 | 0.0 | 4.8 | 4.2 | 14.7 | 10.1 | 3.7 | 4.53 | Promoter (<=1kb) |
| AC019330.1 (chr2) | 198570540 | 198570856 | 317 | 3.2 | 4.0 | 1.8 | 8.0 | 6.3 | 16.0 | 4.03 | Promoter (<=1kb) |
| NRC (chr10) | 3367033 | 3367424 | 392 | 3.2 | 3.6 | 5.6 | 18.4 | 15.1 | 11.9 | 3.98 | Promoter (<=1kb) |
| Y-RNA (chr10) | 15149732 | 15150047 | 316 | 1.7 | 5.6 | 6.5 | 15.6 | 11.1 | 9.2 | 3.86 | Promoter (<=1kb) |
| MIM1 (chr19) | 1354080 | 1354079 | 300 | 6.5 | 1.4 | 6.4 | 19.1 | 14.3 | 8.3 | 3.79 | Promoter (<=1kb) |
| chr8 | 145010797 | 145011845 | 1049 | 23.9 | 17.5 | 7.9 | 42.2 | 45.2 | 39.6 | 3.57 | Promoter (<=1kb) |
| NXN (chr17) | 882709 | 883174 | 466 | 8.7 | 3.9 | 6.4 | 24.7 | 19.0 | 18.5 | 3.54 | Promoter (<=1kb) |

FIG. 7

(A) Subtype B versus A, D, E, F, G

Sequence (5'-3')

| Clade | Accession No. | NF-κb II | NF-κb I | Sp1-III | Sp1-II | Sp1-I |
|---|---|---|---|---|---|---|
| A | AF127566 | CTGGGACTTTCCGCTGGGGACTTTCCAGGAGGCGTGGTTTGGGCGGAGTTGGGAGTGGCT | | | | |
| B | K02013.1 | AAGGGACTTTCCGCTGGGGACTTTCCAGG_GAGGCGTGGCCTGGCGTGGGGACTGGGGAGTGGCG | | | | |
| D | AF127569 | AAGGGACTTTCCGCTGGGGACTTTCCAGG_GAGGCGTGGGACTGGGGACTGGGGAGTGGCT | | | | |
| E | AF127570 | CTAGGACTT_CCGCTGGGGACTTTCCAGGGAGAGGTGTGGCGAGTGGGGAGTGGCT | | | | |
| F | AF127571 | AAGGGACTTTCCGCTGGGGACTTTCCAGAGAGGGCGGTCCAG_AGGGCGGGAGTGGCT | | | | |
| G | AF127572 | AAGGGACTTTCCGCCTGGGGACTTTCC_GGG_AAGCCCCGCCTGGAAGGGG_CTGGGAATTGGCT | | | | |
| | ZFN-B site | CTTTCCGCTGGGGACTTTCCA | | | | |

(B) Subtype B versus C

Sequence (5'-3')

| Clade | Accession No. | NF-κb III | NF-κb II | NF-κb I | Sp1-III | Sp1-II | Sp1-I |
|---|---|---|---|---|---|---|---|
| B | K02013.1 | TG_ | CTTGCTACAAGGGACTTTCCGCTGGGGACTTTCCAGGGAGGCGTGGCCTGGCGTGGGGACTGGGGAGTGGCG | | | | |
| C | AF127567 | | AAGGGACTTTCCGCTGGG_ACTTTCCACTGGGGCG_TTCCAG_GAGGTGGTCAGGGCGGGGACTGGGGACTGGGGAGTGGCC | | | | |
| | ZFN-B site B | | CTTTCCGCTGGGGACTTTCCA | | | | |
| | ZFN-B site C | | CTTTCCGCTGGGGACTTTCCA | | | | |

FIG. 9

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 1
ctttccgctg gggactttcc a                                              21

<210> SEQ ID NO 2
<211> LENGTH: 343
<212> TYPE: DNA
<213> ORGANISM: Artificial sequence
<220> FEATURE:
<223> OTHER INFORMATION: Synthetic polynucleotide

<400> SEQUENCE: 2
aatgaaggag agaacaacag cttgttacac cctatgagcc agcatgggat ggaggacccg      60
gagggagaag tattagtgtg gaagtttgac agcctcctag catttcgtca catggcccga     120
gagctgcatc cggagtacta caaagactgc tgacatcaga cttttctacaa gggacttttcc    180 gctggggact ttccagggag gtgtggcctg ggcgggactg ggagtggcg agccctcaga     240 tgctacatat aagcagctgc tttttgcctg tactgggtct ctctggttag accagatctg     300
agcctgggag ctctctggct aactagggaa cccactgctt aag                      343

<210> SEQ ID NO 3
<211> LENGTH: 645
<212> TYPE: DNA
<213> ORGANISM: Artificial sequence
<220> FEATURE:
<223> OTHER INFORMATION: Synthetic polynucleotide

<400> SEQUENCE: 3
ctcgaacctg ggagaaaacc ctacaagtgc cccgaatgcg ggaaaagctt ctcacgcaag     60
```

```
gacaatctca agaatcacca gcggacgcac accggagaga agccctacaa gtgccccgaa      120
tgcggaaaat cattctcaca acgcgcccac ttggaacgcc accagagaac acacacaggg      180
gagaagccat acaagtgccc tgaatgcggc aagtctttca gtgaaaggtc ccatctgcga      240
gagcaccagc gaacacatac tggcgagaag ccgtacaagt gtcccgagtg cggcaagagt      300
tttagttcca aaaaacacct ggccgaacat cagcggactc acacagggga agccctat       360 aaatgccccg agtgcggcaa gagctttagc gatcccgggg ccctcgtccg acatcagagg      420
acccacacag gggagaaacc ttacaagtgt cctgaatgcg gcaaatcttt cagccagaga      480
gcaaacctgc gagctcacca gagaacccat actggcgaaa agccttataa atgcccgaa       540 tgcgggaaga gtttcagccg ctctgaccac ctgactactc accagcggac acacactggg      600
aagaaaacta gcagcgctgc tgaccccaag aagaagagga aggtg                     645

<210> SEQ ID NO 4
<211> LENGTH: 1659
<212> TYPE: DNA
<213> ORGANISM: Artificial sequence
<220> FEATURE:
<223> OTHER INFORMATION: Synthetic polynucleotide

<400> SEQUENCE: 4
tcgccaggga tccgtcgact tgacgcgttg atatcaacaa gtttgtacaa aaaagcaggc       60
tacaaagagg ccagcggttc cggacgggct gacgcattgg acgattttga tctggatatg      120 ctggaagtg acgcccctcga tgattttgac cttgacatgc ttggttcgga tgcccttgat      180
gactttgacc tcgacatgct cggcagtgac gcccttgatg atttcgacct ggacatgctg      240
attaactcta gaagttccgg atctccgaaa aagaaacgca aagttggtag ccagtacctg      300
cccgacaccg acgaccggca ccggatcgag gaaaagcgga agcggaccta cgagacattc      360
aagagcatca tgaagaagtc ccccttcagc ggccccaccg acctagacc tccacctaga      420 agaatcgccg tgcccagcag atccagcgcc agcgtgccaa acctgcccc ccagccttac       480 cccttcacca gcagcctgag caccatcaac tacgacgagt ccctaccat ggtgttcccc       540 agcggccaga tctctcaggc ctctgctctg gctccagccc ctcctcaggt gctgcctcag      600
gctcctgctc ctgcaccagc tccagccatg gtgtctgcac tggctcaggc accagcaccc      660
gtgcctgtgc tggctcctgg acctccacag gctgtggctc caccagcccc taaacctaca      720
caggccggcg agggcacact gtctgaagct ctgctgcagc tgcagttcga cgacgaggat      780
ctgggagccc tgctgggaaa cagcaccgat cctgccgtgt tcaccgacct ggccagcgtg      840
gacaacagcg agttccagca gctgctgaac cagggcatcc ctgtggcccc tcacaccacc      900
gagcccatgc tgatggaata ccccgaggcc atcacccggc tcgtgacagg cgctcagagg      960
cctcctgatc cagctcctgc ccctctggga gcaccaggcc tgcctaatgg actgctgtct     1020
ggcgacgagg acttcagctc tatcgccgat atggatttct cagccttgct gggctctggc     1080
agcggcagcc gggattccag ggaagggatg tttttgccga agcctgaggc cggctccgct     1140
attagtgacg tgtttgaggg ccgcgaggtg tgccagccaa aacgaatccg gccatttcat     1200
cctccaggaa gtccatgggc caaccgccca ctccccgcca gcctcgcacc aacaccaacc     1260
ggtccagtac atgagccagt cgggtcactg accccggcac cagtccctca gccactggat     1320
ccagcgcccg cagtgactcc cgaggccagt cacctgttgg aggatcccga tgaagagacg     1380
agccaggctg tcaaagccct tcgggagatg gccgatactg tgattcccca gaaggaagag     1440
```

```
gctgcaatct gtggccaaat ggacctttcc catccgcccc caaggggcca tctggatgag    1500
ctgacaacca cacttgagtc catgaccgag gatctgaacc tggactcacc cctgaccccg    1560
gaattgaacg agattctgga taccttcctg aacgacgagt gcctcttgca tgccatgcat    1620
atcagcacag gactgtccat cttcgacaca tctctgttt                           1659
```

<210> SEQ ID NO 5
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 5

```
ggccgtaaaa aacgtcgtca gcgccgtcgc gtcgacctt                             39
```

<210> SEQ ID NO 6
<211> LENGTH: 48
<212> TYPE: DNA
<213> ORGANISM: Artificial sequence
<220> FEATURE:
<223> OTHER INFORMATION: Synthetic polynucleotide

<400> SEQUENCE: 6

```
aagcgacctg ccgccacaaa gaaggctgga caggctaaga agaagaaa                   48
```

<210> SEQ ID NO 7
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 7

```
gagcagaagc tgatctcaga ggaggacctg ctt                                   33
```

<210> SEQ ID NO 8
<211> LENGTH: 2385
<212> TYPE: DNA
<213> ORGANISM: Artificial sequence
<220> FEATURE:
<223> OTHER INFORMATION: Synthetic polynucleotide

<400> SEQUENCE: 8

```
gagcagaagc tgatctcaga ggaggacctg cttaagcgac ctgccgccac aaagaaggct     60
ggacaggcta agaagaagaa actcgaacct ggggagaaac cctacaagtg ccccgaatgc    120
gggaaaagct tctcacgcaa ggacaatctc aagaatcacc agcggacgca caccggagag    180
aagccctaca gtgccccgga tgcggaaaaa tcattctcac aacgcgccca cttggaacgc    240
caccagagaa cacacacagg ggagaagcca tacaagtgcc ctgaatgcgg caagtctttc    300
agtgaaaggt cccatctgcg agagcaccag cgaacacata ctggcgagaa gccgtacaag    360
tgtcccgagt gcggcaagag ttttagttcc aaaaaacacc tggccgaaca tcagcggact    420
cacacagggg agaagcccta taaatgcccc gagtgcggca agagctttag cgatcccggg    480
gccctcgtcc gacatcagag gacccacaca ggggagaaac cttacaagtg tcctgaatgc    540
ggcaaatctt tcagccagag agcaaacctg cgagctcacc agagaaccca tactggcgaa    600
aagccttata atgccctga tgcgggaag agtttcagcc gctctgacca cctgactact    660
caccagcgga cacacactgg gaagaaaact agcagcgctg ctgaccccaa gaagaagagg    720
aaggtgtcgc cagggatccg tcgacttgac gcgttgatat caacaagttt gtacaaaaaa    780
```

```
gcaggctaca aagaggccag cggttccgga cgggctgacg cattggacga ttttgatctg    840
gatatgctgg gaagtgacgc cctcgatgat tttgaccttg acatgcttgg ttcggatgcc    900
cttgatgact ttgacctcga catgctcggc agtgacgccc ttgatgattt cgacctggac    960
atgctgatta actctagaag ttccggatct ccgaaaaaga aacgcaaagt tggtagccag   1020
tacctgcccg acaccgacga ccggcaccgg atcgaggaaa gcggaagcg acctacgag    1080 acattcaaga gcatcatgaa gaagtccccc ttcagcggcc ccaccgaccc tagacctcca   1140
cctagaagaa tcgccgtgcc cagcagatcc agcgccagcg tgccaaaacc tgcccccag    1200 ccttacccct tcaccagcag cctgagcacc atcaactacg acgagttccc taccatggtg   1260
ttccccagcg gccagatctc tcaggcctct gctctggctc cagcccctcc tcaggtgctg   1320
cctcaggctc ctgctcctgc accagctcca gccatggtgt ctgcactggc tcaggcacca   1380
gcacccgtgc ctgtgctggc tcctggacct ccacaggctg tggctccacc agcccctaaa   1440
cctacacagg ccggcgaggg cacactgtct gaagctctgc tgcagctgca gttcgacgac   1500
gaggatctgg agccctgct gggaaacagc accgatcctg ccgtgttcac cgacctggcc   1560
agcgtggaca cagcgagtt ccagcagctg ctgaaccagg gcatccctgt ggcccctcac   1620
accaccgagc ccatgctgat ggaatacccc gaggccatca cccggctcgt gacaggcgct   1680
cagaggcctc ctgatccagc tcctgcccct ctgggagcac caggcctgcc taatggactg   1740
ctgtctggcg acgaggactt cagctctatc gccgatatgg atttctcagc cttgctgggc   1800
tctggcagcg gcagccggga ttccagggaa gggatgtttt tgccgaagcc tgaggccggc   1860
tccgctatta gtgacgtgtt tgagggccgc gaggtgtgcc agccaaaacg aatccggcca   1920
tttcatcctc caggaagtcc atgggccaac cgcccactcc ccgccagcct cgcaccaaca   1980
ccaaccggtc cagtacatga gccagtcggg tcactgaccc cggcaccagt ccctcagcca   2040
ctggatccag cgcccgcagt gactcccgag gccagtcacc tgttggagga tcccgatgaa   2100
gagacgagcc aggctgtcaa agcccttcgg gagatggccg atactgtgat tccccagaag   2160
gaagaggctg caatctgtgg ccaaatgac cttttcccatc cgcccccaag gggccatctg   2220
gatgagctga caaccacact tgagtccatg accgaggatc tgaacctgga ctcacccctg   2280
accccggaat tgaacgagat tctggatacc ttcctgaacg acgagtgcct cttgcatgcc   2340
atgcatatca gcacaggact gtccatcttc gacacatctc tgttt               2385
```

<210> SEQ ID NO 9
<211> LENGTH: 2424
<212> TYPE: DNA
<213> ORGANISM: Artificial sequence
<220> FEATURE:
<223> OTHER INFORMATION: Synthetic polynucleotide

<400> SEQUENCE: 9

```
ggccgtaaaa aacgtcgtca gcgccgtcgc gtcgaccttg agcagaagct gatctcagag     60
gaggacctgc ttaagcgacc tgccgccaca aagaaggctg acaggctaa gaagaagaaa    120 ctcgaacctg gggagaaacc ctacaagtgc cccgaatgcg ggaaaagctt ctcacgcaag    180
gacaatctca gaatcacca gcggacgcac accgagagaa gcccctacaa gtgccccgaa    240
tgcggaaaat cattctcaca acgcgcccac ttggaacgcc accagagaac acacacaggg    300
gagaagccat acaagtgccc tgaatgcggc aagtctttca gtgaaaggtc ccatctgcga    360
gagcaccagc gaacacatac tggcgagaag ccgtacaagt gtcccgagtg cggcaagagt    420
```

```
tttagttcca aaaacaccct ggccgaacat cagcggactc acacagggga gaagccctat    480
aaatgccccg agtgcggcaa gagctttagc gatcccgggg ccctcgtccg acatcagagg    540
acccacacag gggagaaacc ttacaagtgt cctgaatgcg gcaaatcttt cagccagaga    600
gcaaacctgc gagctcacca gagaacccat actggcgaaa agccttataa atgccctgaa    660
tgcgggaaga gtttcagccg ctctgaccac ctgactactc accagcggac acacactggg    720
aagaaaacta gcagcgctgc tgaccccaag aagaagagga aggtgtcgcc agggatccgt    780
cgacttgacg cgttgatatc aacaagtttg tacaaaaaag caggctacaa agaggccagc    840
ggttccggac gggctgacgc attggacgat tttgatctgg atatgctggg aagtgacgcc    900
ctcgatgatt ttgaccttga catgcttggt tcggatgccc ttgatgactt tgacctcgac    960
atgctcggca gtgacgccct tgatgatttc gacctggaca tgctgattaa ctctagaagt    1020
tccggatctc cgaaaaagaa acgcaaagtt ggtagccagt acctgcccga caccgacgac    1080
cggcaccgga tcgaggaaaa gcggaagcgg acctacagag cattcaagag catcatgaag    1140 aagtcccccct tcagcggccc caccgaccct agacctccac ctagaagaat cgccgtgccc    1200
agcagatcca gcgccagcgt gccaaaacct gcccccccagc cttacccctt caccagcagc    1260
ctgagcacca tcaactacga cgagttccct accatggtgt tccccagcgg ccagatctct    1320
caggcctctg ctctggctcc agcccctcct caggtgctgc ctcaggctcc tgctcctgca    1380
ccagctccag ccatggtgtc tgcactggct caggcaccag cacccgtgcc tgtgctggct    1440
cctggacctc cacaggctgt ggctccacca gcccctaaac ctacacaggc cggcgagggc    1500
acactgtctg aagctctgct gcagctgcag ttcgacgacg aggatctggg agccctgctg    1560
ggaaacagca ccgatcctgc cgtgttcacc gacctggcca gcgtggacaa cagcgagttc    1620
cagcagctgc tgaaccaggg catccctgtg gcccctcaca ccaccgagcc catgctgatg    1680
gaataccccg aggccatcac ccggctcgtg acaggcgctc agaggcctcc tgatccagct    1740 cctgccccctc tgggagcacc aggcctgcct aatggactgc tgtctggcga cgaggacttc    1800
agctctatcg ccgatatgga tttctcagcc ttgctgggct ctggcagcgg cagccgggat    1860
tccagggaag ggatgttttt gccgaagcct gaggccggct ccgctattag tgacgtgttt    1920
gagggccgcg aggtgtgcca gccaaaacga atccggccat tcatcctcc aggaagtcca    1980 tgggccaacc gcccactccc cgccagcctc gcaccaacac caaccggtcc agtacatgag    2040
ccagtcgggt cactgacccc ggcaccagtc cctcagccac tggatccagc gcccgcagtg    2100
actcccgagg ccagtcacct gttggaggat cccgatgaag agacgagcca ggctgtcaaa    2160
gcccttcggg agatggccga tactgtgatt ccccagaagg aagaggctgc aatctgtggc    2220
caaatggacc tttcccatcc gcccccaagg ggccatctgg atgagctgac aaccacactt    2280
gagtccatga ccgaggatct gaacctggac tcaccctga cccggaatt gaacgagatt    2340 ctggataccct tcctgaacga cgagtgcctc ttgcatgcca tgcatatcag cacaggactg    2400
tccatcttcg acacatctct gttt    2424
```

<210> SEQ ID NO 10
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 10
tttccgctgg ggactttcca g    21

```
<210> SEQ ID NO 11
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 11
actcaaggca agctttattg aggc                                          24

<210> SEQ ID NO 12
<211> LENGTH: 215
<212> TYPE: PRT
<213> ORGANISM: Artificial sequence
<220> FEATURE:
<223> OTHER INFORMATION: Synthetic polypeptide

<400> SEQUENCE: 12
```

Leu Glu Pro Gly Glu Lys Pro Tyr Lys Cys Pro Glu Cys Gly Lys Ser
1               5                   10                  15

Phe Ser Arg Lys Asp Asn Leu Lys Asn His Gln Arg Thr His Thr Gly
            20                  25                  30

Glu Lys Pro Tyr Lys Cys Pro Glu Cys Gly Lys Ser Phe Ser Gln Arg
        35                  40                  45

Ala His Leu Glu Arg His Gln Arg Thr His Thr Gly Glu Lys Pro Tyr
    50                  55                  60

Lys Cys Pro Glu Cys Gly Lys Ser Phe Ser Glu Arg Ser His Leu Arg
65                  70                  75                  80

Glu His Gln Arg Thr His Thr Gly Glu Lys Pro Tyr Lys Cys Pro Glu
                85                  90                  95

Cys Gly Lys Ser Phe Ser Lys His Leu Ala Glu His Gln Arg
            100                 105                 110

Thr His Thr Gly Glu Lys Pro Tyr Lys Cys Pro Glu Cys Gly Lys Ser
        115                 120                 125

Phe Ser Asp Pro Gly Ala Leu Val Arg His Gln Arg Thr His Thr Gly
    130                 135                 140

Glu Lys Pro Tyr Lys Cys Pro Glu Cys Gly Lys Ser Phe Ser Gln Arg
145                 150                 155                 160

Ala Asn Leu Arg Ala His Gln Arg Thr His Thr Gly Glu Lys Pro Tyr
                165                 170                 175

Lys Cys Pro Glu Cys Gly Lys Ser Phe Ser Arg Ser Asp His Leu Thr
            180                 185                 190

Thr His Gln Arg Thr His Thr Gly Lys Lys Thr Ser Ser Ala Ala Asp
        195                 200                 205

Pro Lys Lys Lys Arg Lys Val
    210                 215

```
<210> SEQ ID NO 13
<211> LENGTH: 553
<212> TYPE: PRT
<213> ORGANISM: Artificial sequence
<220> FEATURE:
<223> OTHER INFORMATION: Synthetic polypeptide

<400> SEQUENCE: 13
```

Ser Pro Gly Ile Arg Arg Leu Asp Ala Leu Ile Ser Thr Ser Leu Tyr
1               5                   10                  15

Lys Lys Ala Gly Tyr Lys Glu Ala Ser Gly Ser Gly Arg Ala Asp Ala

```
                  20                  25                  30
Leu Asp Asp Phe Asp Leu Asp Met Leu Gly Ser Asp Ala Leu Asp Asp
             35                  40                  45
Phe Asp Leu Asp Met Leu Gly Ser Asp Ala Leu Asp Asp Phe Asp Leu
 50                  55                  60
Asp Met Leu Gly Ser Asp Ala Leu Asp Asp Phe Asp Leu Asp Met Leu
 65                  70                  75                  80
Ile Asn Ser Arg Ser Ser Gly Ser Pro Lys Lys Arg Lys Val Gly
             85                  90                  95
Ser Gln Tyr Leu Pro Asp Thr Asp Asp Arg His Arg Ile Glu Glu Lys
            100                 105                 110
Arg Lys Arg Thr Tyr Glu Thr Phe Lys Ser Ile Met Lys Lys Ser Pro
            115                 120                 125
Phe Ser Gly Pro Thr Asp Pro Arg Pro Pro Arg Arg Ile Ala Val
            130                 135                 140
Pro Ser Arg Ser Ser Ala Ser Val Pro Lys Pro Ala Pro Gln Pro Tyr
145                 150                 155                 160
Pro Phe Thr Ser Ser Leu Ser Thr Ile Asn Tyr Asp Glu Phe Pro Thr
                165                 170                 175
Met Val Phe Pro Ser Gly Gln Ile Ser Gln Ala Ser Ala Leu Ala Pro
                180                 185                 190
Ala Pro Pro Gln Val Leu Pro Gln Ala Pro Ala Pro Ala Pro Ala Pro
            195                 200                 205
Ala Met Val Ser Ala Leu Ala Gln Ala Pro Ala Pro Val Pro Val Leu
            210                 215                 220
Ala Pro Gly Pro Pro Gln Ala Val Ala Pro Pro Ala Pro Lys Pro Thr
225                 230                 235                 240
Gln Ala Gly Glu Gly Thr Leu Ser Glu Ala Leu Leu Gln Leu Gln Phe
                245                 250                 255
Asp Asp Glu Asp Leu Gly Ala Leu Leu Gly Asn Ser Thr Asp Pro Ala
            260                 265                 270
Val Phe Thr Asp Leu Ala Ser Val Asp Asn Ser Glu Phe Gln Gln Leu
            275                 280                 285
Leu Asn Gln Gly Ile Pro Val Ala Pro His Thr Thr Glu Pro Met Leu
            290                 295                 300
Met Glu Tyr Pro Glu Ala Ile Thr Arg Leu Val Thr Gly Ala Gln Arg
305                 310                 315                 320
Pro Pro Asp Pro Ala Pro Ala Pro Leu Gly Ala Pro Gly Leu Pro Asn
                325                 330                 335
Gly Leu Leu Ser Gly Asp Glu Asp Phe Ser Ser Ile Ala Asp Met Asp
            340                 345                 350
Phe Ser Ala Leu Leu Gly Ser Gly Ser Gly Ser Arg Asp Ser Arg Glu
            355                 360                 365
Gly Met Phe Leu Pro Lys Pro Glu Ala Gly Ser Ala Ile Ser Asp Val
            370                 375                 380
Phe Glu Gly Arg Glu Val Cys Gln Pro Lys Arg Ile Arg Pro Phe His
385                 390                 395                 400
Pro Pro Gly Ser Pro Trp Ala Asn Arg Pro Leu Pro Ala Ser Leu Ala
            405                 410                 415
Pro Thr Pro Thr Gly Pro Val His Glu Pro Val Gly Ser Leu Thr Pro
            420                 425                 430
Ala Pro Val Pro Gln Pro Leu Asp Pro Ala Pro Ala Val Thr Pro Glu
            435                 440                 445
```

```
Ala Ser His Leu Leu Glu Asp Pro Asp Glu Glu Thr Ser Gln Ala Val
        450                 455                 460
Lys Ala Leu Arg Glu Met Ala Asp Thr Val Ile Pro Gln Lys Glu Glu
465                 470                 475                 480
Ala Ala Ile Cys Gly Gln Met Asp Leu Ser His Pro Pro Arg Gly
            485                 490                 495
His Leu Asp Glu Leu Thr Thr Thr Leu Glu Ser Met Thr Gly Asp Leu
        500                 505                 510
Asn Leu Asp Ser Pro Leu Thr Pro Glu Leu Asn Glu Ile Leu Asp Thr
            515                 520                 525
Phe Leu Asn Asp Glu Cys Leu Leu His Ala Met His Ile Ser Thr Gly
        530                 535                 540
Leu Ser Ile Phe Asp Thr Ser Leu Phe
545                 550
```

<210> SEQ ID NO 14
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 14

```
Gly Arg Lys Lys Arg Arg Gln Arg Arg Val Asp Leu
1               5                   10
```

<210> SEQ ID NO 15
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 15

```
Lys Arg Pro Ala Ala Thr Lys Lys Ala Gly Gln Ala Lys Lys Lys Lys
1               5                   10                  15
```

<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

```
Glu Gln Lys Leu Ile Ser Glu Glu Asp Leu Leu
1               5                   10
```

<210> SEQ ID NO 17
<211> LENGTH: 795
<212> TYPE: PRT
<213> ORGANISM: Artificial sequence
<220> FEATURE:
<223> OTHER INFORMATION: Synthetic polypeptide

<400> SEQUENCE: 17

```
Glu Gln Lys Leu Ile Ser Glu Glu Asp Leu Leu Lys Arg Pro Ala Ala
1               5                   10                  15
Thr Lys Lys Ala Gly Gln Ala Lys Lys Lys Leu Glu Pro Gly Glu
            20                  25                  30
Lys Pro Tyr Lys Cys Pro Glu Cys Gly Lys Ser Phe Ser Arg Lys Asp
        35                  40                  45
```

```
Asn Leu Lys Asn His Gln Arg Thr His Thr Gly Glu Lys Pro Tyr Lys
    50                  55                  60
Cys Pro Glu Cys Gly Lys Ser Phe Ser Gln Arg Ala His Leu Glu Arg
65                  70                  75                  80
His Gln Arg Thr His Thr Gly Glu Lys Pro Tyr Lys Cys Pro Glu Cys
                85                  90                  95
Gly Lys Ser Phe Ser Glu Arg Ser His Leu Arg Glu His Gln Arg Thr
                100                 105                 110
His Thr Gly Glu Lys Pro Tyr Lys Cys Pro Glu Cys Gly Lys Ser Phe
            115                 120                 125
Ser Ser Lys Lys His Leu Ala Glu His Gln Arg Thr His Thr Gly Glu
    130                 135                 140
Lys Pro Tyr Lys Cys Pro Glu Cys Gly Lys Ser Phe Ser Asp Pro Gly
145                 150                 155                 160
Ala Leu Val Arg His Gln Arg Thr His Thr Gly Glu Lys Pro Tyr Lys
                165                 170                 175
Cys Pro Glu Cys Gly Lys Ser Phe Ser Gln Arg Ala Asn Leu Arg Ala
                180                 185                 190
His Gln Arg Thr His Thr Gly Glu Lys Pro Tyr Lys Cys Pro Glu Cys
                195                 200                 205
Gly Lys Ser Phe Ser Arg Ser Asp His Leu Thr Thr His Gln Arg Thr
                210                 215                 220
His Thr Gly Lys Lys Thr Ser Ser Ala Ala Asp Pro Lys Lys Lys Arg
225                 230                 235                 240
Lys Val Ser Pro Gly Ile Arg Arg Leu Asp Ala Leu Ile Ser Thr Ser
                245                 250                 255
Leu Tyr Lys Lys Ala Gly Tyr Lys Glu Ala Ser Gly Ser Gly Arg Ala
                260                 265                 270
Asp Ala Leu Asp Asp Phe Asp Leu Asp Met Leu Gly Ser Asp Ala Leu
                275                 280                 285
Asp Asp Phe Asp Leu Asp Met Leu Gly Ser Asp Ala Leu Asp Asp Phe
            290                 295                 300
Asp Leu Asp Met Leu Gly Ser Asp Ala Leu Asp Asp Phe Asp Leu Asp
305                 310                 315                 320
Met Leu Ile Asn Ser Arg Ser Ser Gly Ser Pro Lys Lys Lys Arg Lys
                325                 330                 335
Val Gly Ser Gln Tyr Leu Pro Asp Thr Asp Asp Arg His Arg Ile Glu
                340                 345                 350
Glu Lys Arg Lys Arg Thr Tyr Glu Thr Phe Lys Ser Ile Met Lys Lys
                355                 360                 365
Ser Pro Phe Ser Gly Pro Thr Asp Pro Arg Pro Pro Arg Arg Ile
                370                 375                 380
Ala Val Pro Ser Arg Ser Ser Ala Ser Val Pro Lys Pro Ala Pro Gln
385                 390                 395                 400
Pro Tyr Pro Phe Thr Ser Ser Leu Ser Thr Ile Asn Tyr Asp Glu Phe
                405                 410                 415
Pro Thr Met Val Phe Pro Ser Gly Gln Ile Ser Gln Ala Ser Ala Leu
                420                 425                 430
Ala Pro Ala Pro Pro Gln Val Leu Pro Gln Ala Pro Ala Pro Ala Pro
            435                 440                 445
Ala Pro Ala Met Val Ser Ala Leu Ala Gln Ala Pro Ala Pro Val Pro
    450                 455                 460
```

```
Val Leu Ala Pro Gly Pro Pro Gln Ala Val Ala Pro Ala Pro Lys
465                 470                 475                 480

Pro Thr Gln Ala Gly Glu Gly Thr Leu Ser Glu Ala Leu Leu Gln Leu
                485                 490                 495

Gln Phe Asp Asp Glu Asp Leu Gly Ala Leu Leu Gly Asn Ser Thr Asp
                500                 505                 510

Pro Ala Val Phe Thr Asp Leu Ala Ser Val Asp Asn Ser Glu Phe Gln
                515                 520                 525

Gln Leu Leu Asn Gln Gly Ile Pro Val Ala Pro His Thr Thr Glu Pro
            530                 535                 540

Met Leu Met Glu Tyr Pro Glu Ala Ile Thr Arg Leu Val Thr Gly Ala
545                 550                 555                 560

Gln Arg Pro Pro Asp Pro Ala Pro Ala Pro Leu Gly Ala Pro Gly Leu
                565                 570                 575

Pro Asn Gly Leu Leu Ser Gly Asp Glu Asp Phe Ser Ser Ile Ala Asp
                580                 585                 590

Met Asp Phe Ser Ala Leu Leu Gly Ser Gly Ser Gly Ser Arg Asp Ser
            595                 600                 605

Arg Glu Gly Met Phe Leu Pro Lys Pro Glu Ala Gly Ser Ala Ile Ser
            610                 615                 620

Asp Val Phe Glu Gly Arg Glu Val Cys Gln Pro Lys Arg Ile Arg Pro
625                 630                 635                 640

Phe His Pro Pro Gly Ser Pro Trp Ala Asn Arg Pro Leu Pro Ala Ser
                645                 650                 655

Leu Ala Pro Thr Pro Thr Gly Pro Val His Glu Pro Val Gly Ser Leu
                660                 665                 670

Thr Pro Ala Pro Val Pro Gln Pro Leu Asp Pro Ala Pro Ala Val Thr
            675                 680                 685

Pro Glu Ala Ser His Leu Leu Glu Asp Pro Asp Glu Glu Thr Ser Gln
690                 695                 700

Ala Val Lys Ala Leu Arg Glu Met Ala Asp Thr Val Ile Pro Gln Lys
705                 710                 715                 720

Glu Glu Ala Ala Ile Cys Gly Gln Met Asp Leu Ser His Pro Pro Pro
                725                 730                 735

Arg Gly His Leu Asp Glu Leu Thr Thr Thr Leu Glu Ser Met Thr Glu
                740                 745                 750

Asp Leu Asn Leu Asp Ser Pro Leu Thr Pro Glu Leu Asn Glu Ile Leu
            755                 760                 765

Asp Thr Phe Leu Asn Asp Glu Cys Leu Leu His Ala Met His Ile Ser
770                 775                 780

Thr Gly Leu Ser Ile Phe Asp Thr Ser Leu Phe
785                 790                 795

<210> SEQ ID NO 18
<211> LENGTH: 808
<212> TYPE: PRT
<213> ORGANISM: Artificial sequence
<220> FEATURE:
<223> OTHER INFORMATION: Synthetic polypeptide

<400> SEQUENCE: 18

Gly Arg Lys Lys Arg Arg Gln Arg Arg Val Asp Leu Glu Gln Lys
1               5                   10                  15

Leu Ile Ser Glu Glu Asp Leu Leu Lys Arg Pro Ala Ala Thr Lys Lys
            20                  25                  30
```

-continued

```
Ala Gly Gln Ala Lys Lys Lys Leu Glu Pro Gly Glu Lys Pro Tyr
            35                  40                  45
Lys Cys Pro Glu Cys Gly Lys Ser Phe Ser Arg Lys Asp Asn Leu Lys
 50                  55                  60
Asn His Gln Arg Thr His Thr Gly Glu Lys Pro Tyr Lys Cys Pro Glu
 65                  70                  75                  80
Cys Gly Lys Ser Phe Ser Gln Arg Ala His Leu Glu Arg His Gln Arg
                 85                  90                  95
Thr His Thr Gly Glu Lys Pro Tyr Lys Cys Pro Glu Cys Gly Lys Ser
                100                 105                 110
Phe Ser Glu Arg Ser His Leu Arg Glu His Gln Arg Thr His Thr Gly
            115                 120                 125
Glu Lys Pro Tyr Lys Cys Pro Glu Cys Gly Lys Ser Phe Ser Ser Lys
        130                 135                 140
Lys His Leu Ala Glu His Gln Arg Thr His Thr Gly Glu Lys Pro Tyr
145                 150                 155                 160
Lys Cys Pro Glu Cys Gly Lys Ser Phe Ser Asp Pro Gly Ala Leu Val
                165                 170                 175
Arg His Gln Arg Thr His Thr Gly Glu Lys Pro Tyr Lys Cys Pro Glu
            180                 185                 190
Cys Gly Lys Ser Phe Ser Gln Arg Ala Asn Leu Arg Ala His Gln Arg
        195                 200                 205
Thr His Thr Gly Glu Lys Pro Tyr Lys Cys Pro Glu Cys Gly Lys Ser
    210                 215                 220
Phe Ser Arg Ser Asp His Leu Thr Thr His Gln Arg Thr His Thr Gly
225                 230                 235                 240
Lys Lys Thr Ser Ser Ala Ala Asp Pro Lys Lys Lys Arg Lys Val Ser
                245                 250                 255
Pro Gly Ile Arg Arg Leu Asp Ala Leu Ile Ser Thr Ser Leu Tyr Lys
            260                 265                 270
Lys Ala Gly Tyr Lys Glu Ala Ser Gly Ser Gly Arg Ala Asp Ala Leu
        275                 280                 285
Asp Asp Phe Asp Leu Asp Met Leu Gly Ser Asp Ala Leu Asp Asp Phe
    290                 295                 300
Asp Leu Asp Met Leu Gly Ser Asp Ala Leu Asp Asp Phe Asp Leu Asp
305                 310                 315                 320
Met Leu Gly Ser Asp Ala Leu Asp Asp Phe Asp Leu Asp Met Leu Ile
                325                 330                 335
Asn Ser Arg Ser Ser Gly Ser Pro Lys Lys Lys Arg Lys Val Gly Ser
            340                 345                 350
Gln Tyr Leu Pro Asp Thr Asp Asp Arg His Arg Ile Glu Glu Lys Arg
        355                 360                 365
Lys Arg Thr Tyr Glu Thr Phe Lys Ser Ile Met Lys Lys Ser Pro Phe
    370                 375                 380
Ser Gly Pro Thr Asp Pro Arg Pro Pro Arg Arg Ile Ala Val Pro
385                 390                 395                 400
Ser Arg Ser Ser Ala Ser Val Pro Lys Pro Ala Pro Gln Pro Tyr Pro
                405                 410                 415
Phe Thr Ser Ser Leu Ser Thr Ile Asn Tyr Asp Glu Phe Pro Thr Met
            420                 425                 430
Val Phe Pro Ser Gly Gln Ile Ser Gln Ala Ser Ala Leu Ala Pro Ala
        435                 440                 445
Pro Pro Gln Val Leu Pro Gln Ala Pro Ala Pro Ala Pro Ala Pro Ala
```

```
                450               455               460
    Met Val Ser Ala Leu Ala Gln Ala Pro Ala Pro Val Pro Val Leu Ala
    465                 470                 475                 480

Pro Gly Pro Pro Gln Ala Val Ala Pro Ala Pro Lys Pro Thr Gln
                    485                 490                 495

Ala Gly Glu Gly Thr Leu Ser Glu Ala Leu Leu Gln Leu Gln Phe Asp
                    500                 505                 510

Asp Glu Asp Leu Gly Ala Leu Leu Gly Asn Ser Thr Asp Pro Ala Val
                    515                 520                 525

Phe Thr Asp Leu Ala Ser Val Asp Asn Ser Glu Phe Gln Gln Leu Leu
    530                 535                 540

Asn Gln Gly Ile Pro Val Ala Pro His Thr Thr Glu Pro Met Leu Met
    545                 550                 555                 560

Glu Tyr Pro Glu Ala Ile Thr Arg Leu Val Thr Gly Ala Gln Arg Pro
                    565                 570                 575

Pro Asp Pro Ala Pro Ala Pro Leu Gly Ala Pro Gly Leu Pro Asn Gly
                    580                 585                 590

Leu Leu Ser Gly Asp Glu Asp Phe Ser Ser Ile Ala Asp Met Asp Phe
                    595                 600                 605

Ser Ala Leu Leu Gly Ser Gly Ser Gly Ser Arg Asp Ser Arg Glu Gly
                    610                 615                 620

Met Phe Leu Pro Lys Pro Glu Ala Gly Ser Ala Ile Ser Asp Val Phe
    625                 630                 635                 640

Glu Gly Arg Glu Val Cys Gln Pro Lys Arg Ile Arg Pro Phe His Pro
                    645                 650                 655

Pro Gly Ser Pro Trp Ala Asn Arg Pro Leu Pro Ala Ser Leu Ala Pro
                    660                 665                 670

Thr Pro Thr Gly Pro Val His Glu Pro Val Gly Ser Leu Thr Pro Ala
                    675                 680                 685

Pro Val Pro Gln Pro Leu Asp Pro Ala Pro Ala Val Thr Pro Glu Ala
                    690                 695                 700

Ser His Leu Leu Glu Asp Pro Asp Glu Glu Thr Ser Gln Ala Val Lys
    705                 710                 715                 720

Ala Leu Arg Glu Met Ala Asp Thr Val Ile Pro Gln Lys Glu Glu Ala
                    725                 730                 735

Ala Ile Cys Gly Gln Met Asp Leu Ser His Pro Pro Arg Gly His
                    740                 745                 750

Leu Asp Glu Leu Thr Thr Thr Leu Glu Ser Met Thr Glu Asp Leu Asn
                    755                 760                 765

Leu Asp Ser Pro Leu Thr Pro Glu Leu Asn Glu Ile Leu Asp Thr Phe
                    770                 775                 780

Leu Asn Asp Glu Cys Leu Leu His Ala Met His Ile Ser Thr Gly Leu
    785                 790                 795                 800

Ser Ile Phe Asp Thr Ser Leu Phe
                    805
```

COMPOSITION AND METHOD FOR ACTIVATING LATENT HUMAN IMMUNODEFICIENCY VIRUS (HIV)

CROSS-REFERENCE TO RELATED APPLICATION

This application is a national stage entry, filed under 35 U.S.C. 371, of International Application No. PCT/US2018/056943, filed Oct. 22, 2018, which claims the benefit of U.S. Provisional Application No. 62/575,307, filed Oct. 20, 2017, the contents of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under P01 AI099783-01 and RO1 AI111139-01 awarded by National Institute of Allergy and Infectious Disease (NIH NIAID). The government has certain rights in the invention.

SEQUENCE LISTING

The Sequence Listing written in file 048440-682001WO_Sequence_Listing_ST25.txt, created on Oct. 22, 2018, 33,250 bytes, machine format IBM-PC, MS-Windows operating system, is hereby incorporated by reference.

BACKGROUND

Complete remedy of HIV infection is often impeded by the presence of latent virus in some cells. The latent virus may stay episomal or integrated into the host cell's genome, remaining transcriptionally inactive provirus. These infected cells that have latent virus can persist for years without producing viral progeny, rendering them refractory to immune surveillance and antiretroviral therapy and providing a reservoir for reactivation and re propagation of HIV. Therefore there is a need to selectively remove such infected cells so as to purge the latent reservoir and completely eradicate infection.

BRIEF SUMMARY

In one aspect, provided herein is a recombinant peptide having a zinc finger domain. The recombinant peptide binds to a target nucleotide sequence and the target nucleotide sequence has the sequence of SEQ ID NO. 1 or a derivative thereof having at least 75% nucleotide sequence identity to the sequence of SEQ ID NO. 1.

In another aspect, provided herein is a nucleotide sequence encoding any of the recombinant peptides of the present disclosure.

In another aspect, provided herein is an expression vector having the foregoing nucleotide sequence that encodes any of the recombinant peptides of the present disclosure.

In another aspect, provided herein is a method of activating a latent HIV from a cell. The method has administering any of the recombinant peptides or any of the expression vectors of the present disclosure to the cell.

In another aspect, provided herein is a method of treating Human Immunodeficiency Virus (HIV) in a subject in need thereof. The method has administering any of the recombinant peptides or any of the expression vectors of the present disclosure to the subject.

BRIEF DESCRIPTION OF THE DRAWINGS

(FIG. 1A) Three iterations of the ZFP-362 recombinant protein were developed. The top candidate ZFP-362, targeted to the LTR-362 site (SEQ ID NO:1) was experimentally tested and redesigned and developed with the TAT peptide, various NLSs and the maltose binding domain (MBP), e.g. made to function as a soluble protein. (FIG. 1B) The ZFP-362-VPR was contrasted with dCas-VPR, found previously to activate latent HIV at levels greater than and more specific than the standard of care latency reactivating drugs. (FIG. 1C) ZFP-362-VPR activates LTR expression of GFP in PMO cells but (FIG. 1D) has no effect on PMO cells containing a deletion in the LTR-362 site (SEQ ID NO:1) targeted by ZFP-362-VPR. For FIGS. 1B-1D, the averages of triplicate treated cells are shown with standard deviations and (*) which represents p<0.001 from a paired T-test.

(FIG. 5A) Venn diagram of distinct and overlapping off-target loci bound by ZFP-362-VPR and gRNA F2-dCas-VPR. (FIG. 5B) Clustering of the ZFP-362-VPR and gRNA F2-dCas-VPR and control pcDNA treated cells. For FIGS. 5A-5B, triplicate treated cells were treated and 72 hrs later CHiP performed with Anti-Myc tag antibody Abcam (ab9132) followed by High throughput deep sequencing.

FIG. 6 shows Table 1, illustrating top ZFP-362-VPR off-target gene promoter bound sites.

FIG. 7 shows Table 2, illustrating top F2-gRNA-362-dCasVPR off-target gene promoter bound sites.

FIG. 9 illustrates alignments between various HIV subtypes relative to subtype B at the LTR-362 site (SEQ ID NO:1) targeted by ZFP-362. Panel (A) shows an alignment of sequences from subtypes A, B, D, E, F, and G. Panel (B) shows an alignment of sequences from subtypes B and C, and illustrates two possible binding sites for ZFP-362. The accession number for each subtype sequence is indicated.

DETAILED DESCRIPTION

Figure 1A:
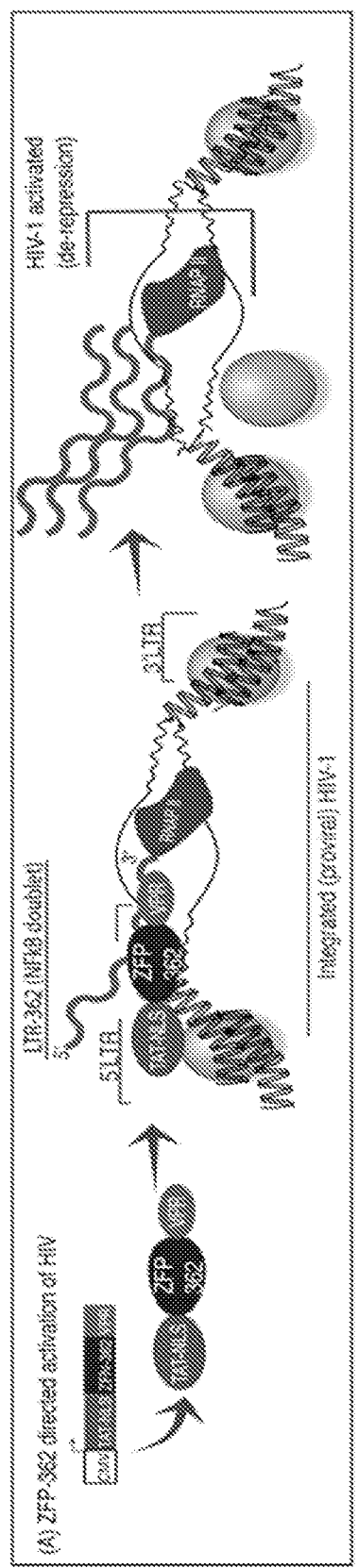
FIGS. 1A-1D: ZFP-362 protein conjugate directed transcriptional activation of latent HIV.

Disclosed herein are, inter alia, compositions and methods for activiating latent Human Immunodeciency Virus (HIV) in cells. In one aspect, the compositions and methods utilize a recombinant peptide that has a DNA-binding, zinc finger domain and a transcription factor (e.g. a transcription activator) that is conjugated to the zinc finger domain. With this configuration, the specific recognition and binding of the zinc finger domain to its target nucleic acid sequence such as a sequence from HIV genome results in recruiting the transcription activator to the HIV genome, activating (e.g. initiating or increasing) the transcription of viral sequences. Also disclosed herein are, inter alia, methods of treating HIV in a subject in need of the treatment. The method may involve activation of latent HIV in cells of the subject and selectively removing such cells from the subject, providing complete and effective treatment of HIV.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

As may be used herein, the terms "nucleic acid," "nucleic acid molecule," "nucleic acid oligomer," "oligonucleotide," "nucleic acid sequence," "nucleic acid fragment," and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof.

Different polynucleotides may have different three-dimensional structures and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may have natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "amino acid sequence," "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

"Percentage of sequence identity" is determined by comparing two optimally aligned sequences over a comparison window, wherein the portion of the polynucleotide or polypeptide sequence in the comparison window may have additions or deletions (i.e., gaps) as compared to the reference sequence (which does not have additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical," "percent identity," "sequence identity," "homology," or "sequence homology" in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

The terms "variant" or "derivative" in the context of polynucleotide (e.g. nucleic acid sequence or oligonucleotide) or peptide (e.g. an amino acid sequence or protein) may refer to a polynucleotide sequence or peptide sequence that has some sequence similarity to their reference sequence. In some examples, a variant or derivative can have at least 30%, 35%, 40%, 45%, 50%, 55%, 60%, 65%, 70%, 75%, 80%, 85%, 90%, 95%, 96%, 97%, 98% or 99% sequence identity (or equivalently used with similarity or homology) to its reference sequence. The terms "functional derivative" or "functional variant" in the context of polynucleotide or peptide sequence may refer to any variant or derivative that maintains the activity to a substantial level, e.g. at least 30% or more of the activity of the reference sequence.

A "vector" as used herein is a nucleic acid molecule that can be used as a vehicle to transfer genetic material into a cell. In embodiments, a vector refers to a DNA molecule harboring at least one origin of replication, a multiple cloning site (MCS) and one or more selection markers. A vector is typically composed of a backbone region and at least one insert or transgene region or a region designed for insertion of a DNA fragment or transgene such as a MCS. The backbone region often contains an origin of replication for propagation in at least one host and one or more selection markers. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment which do not require the use of recombination, transpositions or restriction enzymes (such as, but not limited to, uracil N glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present invention. In embodiments, a vector contains additional features. Such additional features may include natural or synthetic promoters, genetic markers, antibiotic resistance cassettes or selection markers (e.g., toxins such as ccdB or tse2), epitopes or tags for detection, manipulation or purification (e.g., V5 epitope, c-myc, hemagglutinin (HA), FLAG™, polyhistidine (His), glutathione-S-transferase (GST), maltose binding protein (MBP)), scaffold attachment regions (SARs) or reporter genes (e.g., green fluorescent protein (GFP), red fluorescence protein (RFP), luciferase, β-galactosidase etc.). In embodiments, vectors are used to isolate, multiply or express inserted DNA fragments in a target host.

An "expression vector" is designed for expression of a transgene and generally harbors at least one promoter sequence that drives expression of the transgene. Expression as used herein refers to transcription of a transgene or transcription and translation of an open reading frame and can occur in a cell-free environment such as a cell-free expression system or in a host cell. In embodiments expression of an open reading frame or a gene results in the production of a polypeptide or protein. An expression vector is typically designed to contain one or more regulatory sequences such as enhancer, promoter and terminator regions that control expression of the inserted transgene. Suitable expression vectors include, without limitation, plasmids and viral vectors. Vectors and expression systems for various applications are available from commercial suppliers such as Novagen (Madison, Wis.), Clontech (Palo Alto, Calif.), Stratagene (La Jolla, Calif.), and Life Technologies Corp. (Carlsbad, Calif.).

A "promoter" as used herein is a transcription regulatory sequence which is capable of directing transcription of a nucleic acid segment (e.g., a transgene having, for example, an open reading frame) when operably connected thereto. The choice of a promoter to be included in an expression vector depends upon several factors, including without limitation efficiency, selectability, inducibility, desired expression level, and cell or tissue specificity. For example, tissue-, organ- and cell-specific promoters that confer transcription only or predominantly in a particular tissue, organ, and cell type, respectively, can be used. Other classes of promoters include, but are not limited to, inducible promoters, such as promoters that confer transcription in response to external stimuli such as chemical agents, developmental stimuli, or environmental stimuli. Inducible promoters may be induced by pathogens or stress like cold, heat, UV light, or high ionic concentrations or may be induced by chemicals. Examples of inducible promoters are the eukaryotic metallothionein promoter, which is induced by increased levels of heavy metals; the prokaryotic lacL promoter, which is induced in response to isopropyl-β-D-thiogalacto-pyranoside (IPTG); and eukaryotic heat shock promoters, which are induced by raised temperature. Numerous additional bacterial and eukaryotic promoters suitable for use with the invention are known in the art and described in, e.g., in Sambrook et al., Molecular Cloning, A Laboratory Manual (2nd ed. 1989; 3rd ed., 2001); Kriegler, Gene Transfer and Expression: A Laboratory Manual (1990); and Ausubel et al., Current Protocols in Molecular Biology. Bacterial expression systems for expressing the ZFP are available in, e.g., *E. coli, Bacillus* sp., and *Salmonella* (Palva et al. Secretion of interferon by *Bacillus subtilis*. Gene 22:229-235 (1983)). Kits for such expression systems are commercially available. Eukaryotic expression systems for mammalian cells, yeast, and insect cells are well known by those of skill in the art and are also commercially available.

Common promoters for prokaryotic protein expression are e.g., lac promoter or trc and tac promoter (IPTG induction), tetA promoter/operator (anhydrotetracyclin induction), PPBAD promoter (L-arabinose induction), r/zaPBAD promoter (L-rhamnose induction) or phage promoters such as phage promoter pL (temperature shift sensitive), T7, T3, SP6, or T5.

Common promoters for mammalian protein expression are, e.g., Cytomegalovirus (CMV) promoter, H1 promoter, EF1 alpha promoter, SV40 promoter/enhancer, Vaccinia virus promoter, Viral LTRs (MMTV, RSV, HIV etc.), E1B promoter, promoters of constitutively expressed genes (actin, GAPDH), promoters of genes expressed in a tissue-specific manner (albumin, NSE), promoters of inducible genes (Metallothionein, steroid hormones).

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In embodiments, the nucleic acid or protein is at least 50% pure, optionally at least 65% pure, optionally at least 75% pure, optionally at least 85% pure, optionally at least 95% pure, and optionally at least 99% pure.

As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Examples of recombination proteins include Cre, Int, IHF, Xis, Flp, Fis, Hin, Gin, Phi-C31, CM, Tn3 resolvase, TndX, XerC, XerD, TnpX, Hjc, SpCCEl, and Par A.

As used herein, the term "conjugate" refers to the association between atoms or molecules. The association can be direct or indirect. For example, a conjugate between a first moiety (e.g., DNA binding domain) and a second moiety (e.g. a transcriptional modulator such as transcription activator) provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). In embodiments, a first moiety and a second moiety in a conjugate are linked via a peptide linker, e.g. a polymer of amino acids having about 1 to 300 amino acids. Some examples of such a linker include one or more repeat of glycine and serine, e.g. (Gly-Gly-Gly-Ser)n, wherein n is 1 or higher integer. Any linkers known in the art (e.g. see parts.igem.org/Protein domains/Linker) can be used in the recombinant peptides and conjugates of the disclosure. Alternatively, first and second moieties in a conjugate are linked directly without any linking amino acids. These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

The term "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The terms "transfection," "transduction," "transfecting," or "transducing" can be used interchangeably and are defined as a process of introducing a nucleic acid molecule and/or a protein to a cell. Nucleic acids may be introduced to a cell using various methods. The nucleic acid molecule can be a sequence encoding complete proteins or functional portions thereof. Typically, a nucleic acid vector, comprising the elements necessary for protein expression (e.g., a promoter, transcription start site, etc.). Exemplary transfection methods include calcium phosphate transfection, liposomal transfection, nucleofection, sonoporation, transfection through heat shock, magnetifection and electroporation. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

As used herein, the terms "specific binding," "specifically bind," or "specifically binds" refer to two molecules (e.g., DNA-binding domain and its specific binding (or targeting) nucleic acid sequence) that bind to each other with a higher affinity and specificity than a binding between random (e.g. non-target) molecules.

As used herein, the phrase "recognition sequence," "recognition site," "target sequence" or "target site" refers to a particular sequence to which a protein, chemical compound, DNA, or RNA molecule (e.g., a DNA binding domain such as zinc finger domain) recognizes and binds. A recognition sequence or target sequence may refer to a nucleic acid sequence, DNA or RNA, that is recognized and bound by a recombinant peptide with specificity. In certain examples, the recognition sequence or target sequence may be a nucleic acid sequence from HIV genome that is either integrated into the host cell's genome or present as a separate nucleic acid molecule (i.e. episome). Therefore, in some examples where the recombinant peptide has transcription activity, the transcription of the recognition sequence (or the target sequence) or a sequence having the recognition sequence (or the target sequence) can be activated by the recombinant peptide.

As defined herein, the term "activation," "activate," "activating" and the like in reference to gene expression or transcription refers to conversion of a gene or nucleic acid sequence to be transcribed to its complementary RNA (e.g. mRNA) from an initially inactive or deactivated state. In some cases, the gene or nucleic acid sequence that is normally transcribed to a certain extent is activated such that its transcription level is enhanced or increased as compared to its normal level of transcription.

The term "activation," "activate," "activating," "reactivation," "reactivate," "reactivating" and the like used in the context of virus infection refers to enhancing, promoting, stimulating or increasing the activity of the virus including the transcriptional activation of viral gene(s) or genome. Especially in the context of activation or reactivation of latent virus, the term may refer to (i) initiation of transcription of certain viral genes that were previously transcriptionally inactive, (ii) increase of existing transcription of viral genes and/or (iii) transcription of a viral genome. With this activation or reactivation, the latent virus may become transcriptionally active, replicating the viral genome and producing viral progenies such that the virus is no longer in the latency and enters into the lytic cycle.

"Treating" and "treatment" as used herein include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment may increase or decrease over the course of a particular treatment. Changes in dosage may result and become apparent by standard diagnostic assays known in the art. In some instances, chronic administration may be required. For example, the compositions are administered to the subject in an amount and for a duration sufficient to treat the patient.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In embodiments, a patient is human.

A "effective amount" is an amount sufficient for a compound to accomplish a stated purpose relative to the absence of the compound (e.g. achieve the effect for which it is administered, treat a disease or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

Dosages may be varied depending upon the requirements of the patient and the compound being employed. The dose administered to a patient, in the context of the present disclosure, should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this document, unless the context requires otherwise, the words "comprise," "comprising," "contain," "containing," "have," "having," "include," or "including" will be understood to imply the inclusion of a stated step or element or group of steps or elements but not the exclusion of any other step or element or group of steps or elements.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Certain virus has two cycles of reproduction which are the lytic cycle and lysogenic cycles. The lytic cycle results in the destruction of the infected cell and its membrane. One of major differences between the lytic and lysogenic phage cycles is that in the lytic phage, the viral DNA may exist as a separate molecule within the bacterial cell, and replicates separately from the host bacterial DNA. The location of viral DNA in the lysogenic phage cycle may be within the host DNA, therefore in both cases the virus/phage replicates using the host DNA machinery, but in the lytic phage cycle, the phage is a free floating separate molecule to the host DNA. However, in some cases, even during the lysogenic cycle, the viral genome is not integrated into the host DNA but exists as a separate molecule as an episome. When the virus is in lysogeny or lysogenic cycle, the host cell can continue to live and reproduce normally. The genetic material of the virus in the lysogenic cycle, i.e. latent virus, can be transmitted to daughter cells at each subsequent cell division, and at later events (such as UV radiation or the presence of certain chemicals) can release it, causing proliferation of new phages via the lytic cycle.

Virus latency (or viral latency) is the ability of a pathogenic virus to lie dormant (latent) within a cell, denoted as the lysogenic part of the viral life cycle. Latency is often the phase in certain viruses' life cycles in which, after initial infection, proliferation of virus particles ceases. However, the viral genome is not fully eradicated. The result of this is that the virus can reactivate and begin producing large amounts of viral progeny without the host being infected by new outside virus, denoted as the lytic part of the viral life cycle, and stays within the host for a long period or even indefinitely.

Depending on the location of the viral genome in the host cell during the latency, there are generally two types of latency, episomal latency and proviral latency. Episomal latency refers to the use of genetic episomes during latency. In this type, viral genes are stabilized floating in the cytoplasm or nucleus as distinct objects, both as linear or lariat structures. Alternatively, the latent virus can be a provirus that is a virus genome which is integrated into the DNA of a host cell.

One of the well-known virus for the latent capability is HIV. In the proviral latency, HIV uses reverse transcriptase to create a DNA copy of its RNA genome. This allows the virus to largely avoid the immune system. Like other viruses that go latent, it does not typically cause symptoms while latent. Unfortunately, HIV in proviral latency is nearly impossible to target with existing antiretroviral drugs. Given the latent HIV can be active and pathogenic, i.e. entering into lytic cycle later times, the patient with the latent virus in his or her system still has a risk of suffering from pathogenic, reactivated HIV infection at later times. Therefore, removing such infected cells from the patient's system is important in order to completely and effectively treat HIV in the patient.

In embodiments, provided is an engineered transcriptional activation system and method based on a recombinant zinc finger peptide which can selectively activate HIV viral gene transcription and expression in cells of HIV latency. In embodiments, the system and method utilize a recombinant peptide having a zinc finger domain and a transcription activator. In embodiments, the zinc finger domain targets (or binds to) a sequence of HIV genome. This specific recognition of, and binding to, the HIV sequence by the zinc finger domain results in recruiting the conjugated transcription activator to the latent HIV genome, activating the transcription of HIV gene(s) and reactivating the latent HIV. In embodiments, the system and method are effective tools for inducing latent HIV transcription and expression and that their use. In embodiments, the system and method may be used in combination with antiretroviral therapy to provide improved therapies for HIV infection. In embodiments, the HIV is an HIV subtype of A, B, C, D, E, F, or G. In embodiments, the HIV subtype is A or B. A "subtype" may also be referred to as a "clade."

Compositions

In one aspect, the present disclosure provides a recombinant peptide that has a zinc finger domain. A zinc finger domain is used herein according to its plain and ordinary meaning in the art and generally refers to a protein structural domain capable of binding a target nucleic acid sequence. In embodiments, the zinc finger domain coordinates one or more zinc ions in order to stabilize its structure. Zinc finger (Znf) domains may be relatively small protein domains that can contain multiple finger-like protrusions that make tandem contacts with their target molecule. In embodiments, the Znf forms salt bridges to stabilize the finger-like folds. In embodiments, the Znf forms coordinates a metal (e.g. zinc) to stabilize the finger-like folds.

In embodiments, the zinc finger domain that is used in the recombinant peptide of the disclosures recognizes (or binds to) a target nucleic acid sequence with specificity. The target nucleic acid can be DNA or RNA sequence. In embodiments, the target nucleic acid sequence contains the sequence of SEQ ID NO. 1 or a derivative of the sequence of SEQ ID NO. 1. In embodiments, the derivative is a nucleic acid sequence that has at least 50%, 55%, 60%, 65%, 70%, 75%, 80%, 85%, 90%, 95%, 96%, 97%, 98% or 99% sequence identity to the sequence of SEQ ID NO.1. In embodiments, the derivative has at least 90%, 95%, 96%, 97%, 98%, 99% or 100% nucleic acid sequence identity across the whole sequence or a portion of the sequence (e.g. a 5, 10, 15 or 20 continuous nucleic acid portion) compared to SEQ ID NO. 1.

In embodiments, the target nucleic acid sequence of the zinc finger domain has a derivative sequence of the sequence of SEQ ID NO.1, wherein the derivative has at least 85% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 90% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 95% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 96% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 97% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 98% nucleotide sequence identity to the sequence of SEQ ID NO. 1.

In embodiments, the target nucleic acid sequence of the zinc finger domain has a derivative sequence of the sequence of SEQ ID NO.1, wherein the derivative has at least 99% nucleotide sequence identity to the sequence of SEQ ID NO. 1.

In embodiments, the target nucleic acid sequence of the zinc finger domain contains the sequence of SEQ ID NO. 2 or a derivative of the sequence of SEQ ID NO. 2. The derivative herein may refer to a nucleic acid sequence that has the nucleotide sequence identity of at least 50%, 55%, 60%, 65%, 70%, 75%, 80%, 85%, 90%, 95%, 96%, 97%, 98% or 99% to the sequence of SEQ ID NO.2. In embodiments, the derivative has at least 90%, 95%, 96%, 97%, 98%, 99% or 100% nucleic acid sequence identity across the whole sequence or a portion of the sequence (e.g. a 10, 50, 100, 150, 200 or more continuous nucleic acid portion) compared to SEQ ID NO. 2.

In embodiments, the target nucleic acid sequence of the zinc finger domain has a derivative sequence of the sequence of SEQ ID NO.2, wherein the derivative has at least 85% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 90% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 95% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 96% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 97% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 98% nucleotide sequence identity to the sequence of SEQ ID NO. 2.

In embodiments, the target nucleic acid sequence of the zinc finger domain has a derivative sequence of the sequence of SEQ ID NO.2, wherein the derivative has at least 99% nucleotide sequence identity to the sequence of SEQ ID NO. 2.

In embodiments, the zinc finger domain of the recombinant peptide recognizes and binds to a sequence of HIV genome with specificity. In embodiments, the HIV genome sequence that is specifically recognized (or bound) by the zinc finger domain is a long terminal repeat (LTR) of HIV.

Long terminal repeats (LTRs) are used according to their plain and ordinary meaning and the art. Thus, LTR's may contain identical sequences of DNA or RNA that repeat hundreds or thousands of times found at either end of viral retroviral genome or proviral DNA that is formed by reverse transcription of retroviral RNA. They may be used by viruses to insert their genetic material into the host genomes. The LTRs may be partially transcribed into an RNA intermediate, followed by reverse transcription into complementary DNA (cDNA) and ultimately dsDNA (double-stranded DNA) with full LTRs. The LTRs may then mediate integration of the retroviral DNA via an LTR specific integrase into another region of the host chromosome. In the proviral latency, once the provirus has been integrated, the LTR on the 5' end may serve as the promoter for the entire retroviral genome, while the LTR at the 3' end may provide for nascent viral RNA polyadenylation and encodes some accessory proteins. In embodiments, the recombinant peptide of the present disclosure targets (or binds to) 5' LTR, 3' LTR or both.

In embodiments, the zinc finger domain recognizes with specificity (e.g. specifically binds) about 5 bases, about 10 bases, about 15 bases, about 20 bases, about 25 bases, about 30 bases, about 35 bases, about 40 bases, about 45 bases or about 50 bases from the HIV LTR sequence of a recognized sequence (e.g. the target sequence). In embodiments, the zinc finger domain recognizes (e.g. binds to) a derivative of the target sequence which has at least 50%, 55%, 60%, 65%, 70%, 75%, 80%, 85%, 90%, 95%, 96%, 97%, 98% or 99% sequence identify to the target sequence.

In embodiments, the recombinant peptide of the present disclosure includes one or more than one zinc finger domains. In embodiments, the number of zinc finger domains present in a single molecule of the recombinant peptide is 1, 2, 3, 4, 5, 6, 7, 8, 9, 10 or more.

In embodiments, the recombinant peptide having one or more zinc finger domains used in the present disclosure is encoded by the sequence of SEQ ID NO. 3 or a derivative thereof. The sequence of SEQ ID NO. 3 encodes a non-naturally occurring peptide sequence, which may be referred to herein as "ZFP-362" or "ZFP-362 peptide." The amino acid sequence encoded by SEQ ID NO. 3 is shown in SEQ ID NO. 12. In embodiments, the ZFP-362 peptide specifically targets (e.g. specifically binds, or is capable of specifically binding) the HIV LTR including HIV-1 LTR and induces activation of HIV transcription at levels comparable to defective CRISPR VPR conjugates (dCas-VPR) (see FIGS. 1B and 1C). In embodiments, the targeted activation of HIV LTR expression by the ZFP-362 conjugated to VPR (also referred to herein as ZFP-362-VPR), which is further described below, is specifically targeted to the well-defined NF-κB double site, a region known to be susceptible to modulation and control of viral transcription and only found in HIV. In embodiments, targeting of ZFP-362-VPR to cells lacking to the well-defined NF-κB double site are not activated (see FIG. 1D) compared with those containing this site (see FIG. 1C). Therefore, in embodiments, the recombinant peptide of the present disclosure that has the ZFP-362 or derivative thereof can induce transcriptional activation in the cells infected with latent HIV, but not in HIV-free cells. In embodiments, the infected cells from which the latent HIV are activated by the recombinant peptide of the disclosures will be treated, e.g. killed by the action of additional anti-viral drugs.

In embodiments, the recombinant peptide of the present disclosure is encoded by the sequence of SEQ ID NO. 3 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 3. In embodiments, the derivative has at least 90%, 95%, 96%, 97%, 98%, 99% or 100% nucleic acid sequence identity across the whole sequence or a portion of the sequence (e.g. a 20, 50, 100, 150, 200 or more continuous nucleic acid portion) compared to SEQ ID NO. 3. Also, in embodiments, the derivative encodes a functional derivative of the recombinant peptide encoded by SEQ ID NO. 3 that has at least 30%, 35%, 40%, 45%, 50%, 55%, 60%, 65%, 70%, 75%, 80%, 85%, 90%, 95%, 96%, 97%, 98% or 99% of the activity of the peptide encoded by SEQ ID NO. 3 (e.g. the activity of the ZFP-362 that binds to its target nucleic acid sequence with specificity).

In embodiments, the derivative of SEQ ID NO. 3 has at least 75% sequence identity to at least 500 contiguous nucleotides of SEQ ID NO. 3. In embodiments, the derivative has at least 80% sequence identity to at least 400 contiguous nucleotides of SEQ ID NO. 3. In embodiments, the derivative has at least 90% sequence identity to at least 300 contiguous nucleotides of SEQ ID NO. 3. In embodiments, the derivative has at least 95% sequence identity to at least 200 contiguous nucleotides of SEQ ID NO. 3. In embodiments, the derivative has 100% identity to at least 100 contiguous nucleotides of SEQ ID NO. 3. In embodiments, the derivative has one or more conservative modifications of SEQ ID NO. 3 or of the polypeptide it encodes (e.g., 1, 2, 3, 4, 5, 10, 15, 25, 50, 100, 150, 200, or more conservative modifications).

In embodiments, the recombinant peptide of the present disclosure has the sequence of SEQ ID NO. 12 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 12. In embodiments, the derivative has at least 90%, 95%, 96%, 97%, 98%, 99% or 100% sequence identity across the whole sequence or a portion of the sequence (e.g. a 20, 50, 100, 150, 200 or more continuous amino acid portion) compared to SEQ ID NO. 12. Also, in embodiments, the derivative is a functional derivative of the recombinant peptide of SEQ ID NO. 12 that has at least 30%, 35%, 40%, 45%, 50%, 55%, 60%, 65%, 70%, 75%, 80%, 85%, 90%, 95%, 96%, 97%, 98% or 99% of the activity of the polypeptide of SEQ ID NO. 12 (e.g. the activity of the ZFP-362 that binds to its target nucleic acid sequence with specificity).

In embodiments, the derivative of SEQ ID NO. 12 has at least 75% sequence identity to at least 150 contiguous amino acids of SEQ ID NO. 12. In embodiments, the derivative has at least 80% sequence identity to at least 125 contiguous amino acids of SEQ ID NO. 12. In embodiments, the derivative has at least 90% sequence identity to at least 100 contiguous amino acids of SEQ ID NO. 12. In embodiments, the derivative has at least 95% sequence identity to at least 75 contiguous amino acids of SEQ ID NO. 12. In embodiments, the derivative has 100% identity to at least 50 contiguous amino acids of SEQ ID NO. 12. In embodiments, the derivative has one or more conservative modifications of SEQ ID NO. 12 (e.g., 1, 2, 3, 4, 5, 10, 15, 25, 50, or more conservative modifications).

In embodiments, the recombinant peptide of the present disclosure is encoded by the sequence of SEQ ID NO. 3 or a derivative thereof having at least 75% nucleic acid sequence identity to the sequence of SEQ ID NO. 3. In embodiments, the recombinant peptide has the sequence of SEQ ID NO. 12, or a derivative thereof having at least 75% amino acid sequence identity to the sequence of SEQ ID NO. 12.

In embodiments, the recombinant peptide of the present disclosure is encoded by the sequence of SEQ ID NO. 3 or a derivative thereof having at least 80% nucleic acid sequence identity to the sequence of SEQ ID NO. 3. In embodiments, the recombinant peptide has the sequence of SEQ ID NO. 12, or a derivative thereof having at least 80% amino acid sequence identity to the sequence of SEQ ID NO. 12.

In embodiments, the recombinant peptide of the present disclosure is encoded by the sequence of SEQ ID NO. 3 or a derivative thereof having at least 85% nucleic acid sequence identity to the sequence of SEQ ID NO. 3. In embodiments, the recombinant peptide has the sequence of SEQ ID NO. 12, or a derivative thereof having at least 85% amino acid sequence identity to the sequence of SEQ ID NO. 12.

In embodiments, the recombinant peptide of the present disclosure is encoded by the sequence of SEQ ID NO. 3 or a derivative thereof having at least 90% nucleic acid sequence identity to the sequence of SEQ ID NO. 3. In embodiments, the recombinant peptide has the sequence of SEQ ID NO. 12, or a derivative thereof having at least 90% amino acid sequence identity to the sequence of SEQ ID NO. 12.

In embodiments, the recombinant peptide of the present disclosure is encoded by the sequence of SEQ ID NO. 3 or a derivative thereof having at least 95% nucleic acid sequence identity to the sequence of SEQ ID NO. 3. In embodiments, the recombinant peptide has the sequence of SEQ ID NO. 12, or a derivative thereof having at least 95% amino acid sequence identity to the sequence of SEQ ID NO. 12.

In embodiments, the recombinant peptide of the present disclosure is encoded by the sequence of SEQ ID NO. 3 or a derivative thereof having at least 96% nucleic acid sequence identity to the sequence of SEQ ID NO. 3. In embodiments, the recombinant peptide has the sequence of SEQ ID NO. 12, or a derivative thereof having at least 96% amino acid sequence identity to the sequence of SEQ ID NO. 12.

In embodiments, the recombinant peptide of the present disclosure is encoded by the sequence of SEQ ID NO. 3 or a derivative thereof having at least 97% nucleic acid sequence identity to the sequence of SEQ ID NO. 3. In embodiments, the recombinant peptide has the sequence of SEQ ID NO. 12, or a derivative thereof having at least 97% amino acid sequence identity to the sequence of SEQ ID NO. 12.

In embodiments, the recombinant peptide of the present disclosure is encoded by the sequence of SEQ ID NO. 3 or a derivative thereof having at least 98% nucleic acid sequence identity to the sequence of SEQ ID NO. 3. In embodiments, the recombinant peptide has the sequence of SEQ ID NO. 12, or a derivative thereof having at least 98% amino acid sequence identity to the sequence of SEQ ID NO. 12.

In embodiments, the recombinant peptide of the present disclosure is encoded by the sequence of SEQ ID NO. 3 or a derivative thereof having at least 99% nucleic acid sequence identity to the sequence of SEQ ID NO. 3. In embodiments, the recombinant peptide has the sequence of SEQ ID NO. 12, or a derivative thereof having at least 99% amino acid sequence identity to the sequence of SEQ ID NO. 12.

In embodiments, the recombinant peptide has one or more additional components such as additional peptides. In embodiments, the zinc finger domain can form a conjugate with the one or more peptides to form the recombinant peptide of the disclosures. The conjugate can be formed, for example, via a chemical linkage such as a covalent bond or a non-chemical linkage such as ionic binding. In embodiments, the zinc finger domain and the additional peptide can be covalently linked to each other, i.e. forming a fusion protein with or without a sequence linking the two.

In some embodiment, the additional peptide that form a conjugate with the zinc finger domain is a peptide capable of transcriptional activation. In embodiments, the peptide capable of transcriptional activation is a transcriptional activator. A transcriptional activator is a protein (transcription factor) that increases gene transcription of a gene or set of genes. In some cases, transcriptional activators, when recruited to a DNA site, e.g. a promoter of a target sequence for activation, make or enhance protein-protein interactions with the general transcription machinery (e.g. RNA polymerase and general transcription factors), thereby facilitating the binding of the general transcription machinery to the promoter.

Any peptide that is capable of activating transcription (e.g. initiating the transcription of a transcriptionally silent sequence or increasing the transcription of an already transcriptionally active sequence) can be used in the recombinant peptide of the disclosures. In embodiments, the transcriptional activators used in the present disclosure include, but not limited to, viral protein P (VPR), p65 transactivating subunit of NF-kappa B, heat-shock factor 1 (HSF) activation domain, VP64 (tetramer of VP16) activation domain, synergistic activation mediator (SAM) and any derivatives thereof.

VPR is used herein according to its plain and ordinary meaning in the art. In embodiments, the recombinant peptide of the present disclosure includes a VPR peptide or derivative thereof that is capable of transcriptional activation. In embodiments, the VPR is encoded by the sequence of SEQ ID NO. 4 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% of the nucleic acid sequence identity to the sequence of SEQ ID NO. 4. In embodiments, the derivative has at least 90%, 95%, 96%, 97%, 98%, 99% or 100% nucleic acid sequence identity across the whole sequence or a portion of the sequence (e.g. a 20, 50, 100, 150, 200 or more continuous nucleic acid portion) compared to SEQ ID NO. 4. Also, in embodiments, the derivative encodes a functional derivative of VPR that has at least 30%, 35%, 40%, 45%, 50%, 55%, 60%, 65%, 70%, 75%, 80%, 85%, 90%, 95%, 96%, 97%, 98% or 99% of the transcriptional activity of the VPR encoded by SEQ ID NO. 4.

In embodiments, the derivative of SEQ ID NO. 4 has at least 75% sequence identity to at least 1,300 contiguous nucleotides of SEQ ID NO. 4. In embodiments, the derivative has at least 80% sequence identity to at least 1,000 contiguous nucleotides of SEQ ID NO. 4. In embodiments, the derivative has at least 90% sequence identity to at least 750 contiguous nucleotides of SEQ ID NO. 4. In embodiments, the derivative has at least 95% sequence identity to at least 500 contiguous nucleotides of SEQ ID NO. 4. In embodiments, the derivative has 100% sequence identity to at least 250 contiguous nucleotides of SEQ ID NO. 4. In embodiments, the derivative has one or more conservative modifications of SEQ ID NO. 4 or of the polypeptide it encodes (e.g., 1, 2, 3, 4, 5, 10, 15, 25, 50, 100, 150, 200, 300, 500, or more conservative modifications).

In embodiments, the VPR peptide has the sequence of SEQ ID NO. 13 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 13. In embodiments, the derivative has at least 90%, 95%, 96%, 97%, 98%, 99% or 100% sequence identity across the whole sequence or a portion of the sequence (e.g. a 20, 50, 100, 150, 200 or more continuous amino acid portion) compared to SEQ ID NO. 13. Also, in embodiments, the derivative is a functional derivative of the VPR of SEQ ID NO. 13 that has at least 30%, 35%, 40%, 45%, 50%, 55%, 60%, 65%, 70%, 75%, 80%, 85%, 90%, 95%, 96%, 97%, 98% or 99% of the activity of the polypeptide of SEQ ID NO. 13.

In embodiments, the derivative of SEQ ID NO. 13 has at least 75% sequence identity to at least 400 contiguous amino acids of SEQ ID NO. 13. In embodiments, the derivative has at least 80% sequence identity to at least 300 contiguous amino acids of SEQ ID NO. 13. In embodiments, the derivative has at least 90% sequence identity to at least 250 contiguous amino acids of SEQ ID NO. 13. In embodiments, the derivative has at least 95% sequence identity to at least 200 contiguous amino acids of SEQ ID NO. 13. In embodiments, the derivative has 100% identity to at least 100 contiguous amino acids of SEQ ID NO. 13. In embodiments, the derivative has one or more conservative modifications of SEQ ID NO. 13 (e.g., 1, 2, 3, 4, 5, 10, 15, 25, 50, 100, or more conservative modifications).

In embodiments, the ZFP-362 or derivative thereof is conjugated to a transcriptional activator, forming the recombinant peptide of the present disclosure. In embodiments, the ZFP-362 or a derivative thereof is conjugated to a VPR or derivative thereof. In these embodiments, the ZFP-362 specifically binds to its target sequence, e.g. the HIV LRT sequence and this binding will bring the VPR (or derivative thereof) to the LRT sequence, promoting the transcription of LTR and the rest of HIV genome. In embodiments, this specific binding activates HIV latently present in the infected cells. In embodiments, the infected cells are targeted with antiviral drugs in a follow-on treatment.

In embodiments, the recombinant peptide of the present disclosure has further components, which includes, but are not limited to, a cell-penetrating peptide (e.g. a TAT peptide or a derivative thereof) and/or one or more nuclear localization signals. Additionally, a peptide that can promote stabilization of the recombinant protein and/or enhance the protein isolation (e.g. myc-tag sequence and a maltose binding sequence) can also be contained in the recombinant peptide.

Cell-penetrating peptides (CPPs) generally are short peptides that can facilitate cellular intake/uptake of various molecular equipment (e.g. a recombinant peptide). The cargo is associated with the CPPs either through chemical linkage via covalent bonds or through non-covalent interactions. The function of the CPPs is to deliver the cargo into cells. Any peptides that are known to be capable of CPPs or have cell-penetrating activity can be used in the composition and methods of the disclosures. In embodiments, the trans-activating transcriptional activator (TAT), which was initially found as a HIV-1 gene and product thereof, or a derivative of TAT is used as a CPP, thereby enhancing the intake/uptake of the recombinant peptide into the cells. In addition to enhancing the transfer to the nucleus of the cell, the TAT peptide can also facilitate crossing the blood brain barrier, which can further enhance the delivery of the recombinant protein to the cells. In embodiments, the TAT peptide used in the disclosure is encoded by the sequence of SEQ ID NO. 5 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% of the nucleic acid sequence identity to the sequence of SEQ ID NO. 5. In embodiments, the derivative has at least 90%, 95%, 96%, 97%, 98%, 99% or 100% nucleic acid sequence identity across the whole sequence or a portion of the sequence (e.g. a 5, 10, 20, 25 or more continuous nucleic acid portion) compared to SEQ ID NO. 5. Also, in embodiments, the derivative encodes a functional derivative of TAT that has at least 30%, 35%, 40%, 45%, 50%, 55%, 60%, 65%, 70%, 75%, 80%, 85%, 90%, 95%, 96%, 97%, 98% or 99% of the activity of the TAT encoded by SEQ ID NO. 5.

In embodiments, the TAT peptide has the sequence of SEQ ID NO. 14 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 14. In embodiments, the derivative has at least 90%, 95%, 96%, 97%, 98%, 99% or 100% sequence identity across the whole sequence or a portion of the sequence (e.g. a 5, 6, 7, 8, 9, 10, or more continuous amino acid portion) compared to SEQ ID NO. 14. Also, in embodiments, the derivative is a functional derivative of the TAT peptide of SEQ ID NO. 14 that has at least 30%, 35%, 40%, 45%, 50%, 55%, 60%, 65%, 70%, 75%, 80%, 85%, 90%, 95%, 96%, 97%, 98% or 99% of the activity of the polypeptide of SEQ ID NO. 14. In embodiments, the derivative has one or more conservative modifications of SEQ ID NO. 14 (e.g., 1, 2, 3, 4, 5, 10, or more conservative modifications).

A nuclear localization signal or sequence (NLS) is an amino acid sequence that tags a protein for import into the cell nucleus by nuclear transport. Any peptides that are known to be capable of NLS or have nuclear localization activity can be used in the composition and methods of the disclosures. In embodiments, the recombinant protein has one or more NLSs. In embodiments, the number of NLS present in the recombinant peptide can be 1, 2, 3, 4, 5, 6, 7, 8, 9, 10 or more. In embodiments, the NLS used in the disclosure is encoded by the sequence of SEQ ID NO. 6 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% of the nucleic acid sequence identity to the sequence of SEQ ID NO. 6. In embodiments, the derivative has at least 90%, 95%, 96%, 97%, 98%, 99% or 100% nucleic acid sequence identity across the whole sequence or a portion of the sequence (e.g. a 2, 3, 4, 5 or more continuous nucleic acid portion) compared to SEQ ID NO. 6. Also, in embodiments, the derivative encodes a functional derivative of NLS that has at least 30%, 35%, 40%, 45%, 50%, 55%, 60%, 65%, 70%, 75%, 80%, 85%, 90%, 95%, 96%, 97%, 98% or 99% of the activity of the NLS encoded by SEQ ID NO. 6.

In embodiments, the NLS has the sequence of SEQ ID NO: 15 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 15. In embodiments, the derivative has at least 90%, 95%, 96%, 97%, 98%, 99% or 100% sequence identity across the whole sequence or a portion of the sequence (e.g. a 5, 6, 7, 8, 9, 10, or more continuous amino acid portion) compared to SEQ ID NO. 15. Also, in embodiments, the derivative is a functional derivative of the NLS of SEQ ID NO. 15 that has at least 30%, 35%, 40%, 45%, 50%, 55%, 60%, 65%, 70%, 75%, 80%, 85%, 90%, 95%, 96%, 97%, 98% or 99% of the activity of the polypeptide of SEQ ID NO. 15. In embodiments, the derivative has one or more conservative modifications of SEQ ID NO. 15 (e.g., 1, 2, 3, 4, 5, 10, or more conservative modifications).

In embodiments, the recombinant peptide of the present disclosure has one or more additional sequences such as a myc-tag sequence and maltose-binding sequence. A myc tag is a polypeptide protein tag derived from the c-myc gene product that can be added to a protein using recombinant DNA technology. It can be used for affinity chromatography, then used to separate recombinant protein expressed by the host organism. It can also be used in the isolation of protein complexes with multiple subunits. In embodiments, the recombinant peptide has a myc-tag sequence that is encoded by the sequence of SEQ ID NO. 7 or derivative thereof having at least 70%, 75%, 80%, 85%, 90%, 95%, 96%, 97%, 98% or 99% of nucleic acid sequence identity to the sequence of SEQ ID NO. 7. In embodiments, the derivative has at least 90%, 95%, 96%, 97%, 98%, 99% or 100% nucleic acid sequence identity across the whole sequence or a portion of the sequence (e.g. a 2, 3, 4, 5 or more continuous nucleic acid portion) compared to SEQ ID NO. 7. Maltose binding peptide (MBP), which was originally found as an *Escherichia coli* gene and product thereof, can be used to increase the solubility of recombinant proteins. In this system, the protein of interest can be expressed as a MBP-fusion protein, preventing aggregation of the protein of interest. In addition, MBP can also be used as an affinity tag for purification of recombinant proteins. Thus, the MBP-protein fusion can be purified by eluting the column with maltose. Once the fusion protein is obtained in purified form, the protein of interest can often be cleaved from MBP with a specific protease. The protein of interest can then be separated from MBP by affinity chromatography. In embodiments, the recombinant peptide has a MBP sequence that is known in the art or a derivative thereof.

In embodiments, the myc-tag has the sequence of SEQ ID NO. 16 or a derivative thereof. In embodiments, the derivative has at least 30%, 35%, 40%, 45%, 50%, 55%, 60%, 65%, 70%, 75%, 80%, 85%, 90%, 95%, 96%, 97%, 98% or 99% sequence identity to the sequence of SEQ ID NO. 16. In embodiments, the derivative has at least 90%, 95%, 96%, 97%, 98%, 99% or 100% sequence identity across the whole sequence or a portion of the sequence (e.g. a 5, 6, 7, 8, 9, or 10 continuous amino acid portion) compared to SEQ ID NO. 16. Also, in embodiments, the derivative is a functional derivative of the myc-tag of SEQ ID NO. 16 that has at least 30%, 35%, 40%, 45%, 50%, 55%, 60%, 65%, 70%, 75%, 80%, 85%, 90%, 95%, 96%, 97%, 98% or 99% of the activity of the polypeptide of SEQ ID NO. 16. In embodiments, the derivative has one or more conservative modifications of SEQ ID NO. 16 (e.g., 1, 2, 3, 4, 5, or more conservative modifications).

In embodiments, the recombinant peptide of the present disclosure has one or more of the following components: (i) a zinc finger domain (e.g. ZFP-362), (ii) a peptide capable of transcription activation (e.g. a transcription activator), (iii) a cell-penetrating sequence, (iv) nuclear localization sequence and (v) additional sequence for protein stabilization and isolation (or purification). In embodiments, the number of each of the foregoing components present in a single molecule of the recombinant peptide, independently, can be 0, 1, 2, 3, 4, 5, 6, 7, 8, 9, 10 or more.

In embodiments, the recombinant peptide of the present disclosure has (i) a zinc finger domain (e.g. ZFP-362) and (ii) a peptide capable of transcription activation (e.g. a transcription activator).

In embodiments, the recombinant peptide of the present disclosure has (i) a zinc finger domain (e.g. ZFP-362), (ii) a peptide capable of transcription activation (e.g. a transcription activator) and (iii) a cell-penetrating sequence.

In embodiments, the recombinant peptide of the present disclosure has (i) a zinc finger domain (e.g. ZFP-362), (ii) a peptide capable of transcription activation (e.g. a transcription activator) and (iv) nuclear localization sequence.

In embodiments, the recombinant peptide of the present disclosure has (i) a zinc finger domain (e.g. ZFP-362), (ii) a peptide capable of transcription activation (e.g. a transcription activator) and (v) additional sequence for protein stabilization and isolation (or purification).

In embodiments, the recombinant peptide of the present disclosure has (i) a zinc finger domain (e.g. ZFP-362), (ii) a peptide capable of transcription activation (e.g. a transcription activator), (iii) a cell-penetrating sequence and (iv) nuclear localization sequence.

In embodiments, the recombinant peptide of the present disclosure has (i) a zinc finger domain (e.g. ZFP-362), (ii) a peptide capable of transcription activation (e.g. a transcription activator), (iii) a cell-penetrating sequence and (v) additional sequence for protein stabilization and isolation (or purification).

In embodiments, the recombinant peptide of the present disclosure has (i) a zinc finger domain (e.g. ZFP-362), (ii) a peptide capable of transcription activation (e.g. a transcription activator), (iv) nuclear localization sequence and (v) additional sequence for protein stabilization and isolation (or purification). In some of these embodiments, the recombinant peptide has the ZFP-362 as (i), a VPR as (ii), a NLS as (iv) and a myc-tag sequence as (v) as provided in SEQ ID NO. 8. In embodiments, the recombinant polypeptide has the sequence of SEQ ID NO. 17, or a derivative thereof.

In embodiments, the recombinant peptide of the present disclosure has (i) a zinc finger domain (e.g. ZFP-362), (ii) a peptide capable of transcription activation, (iii) a cell-penetrating sequence, (iv) nuclear localization sequence and (v) additional sequence for protein stabilization and isolation (or purification). In some of these embodiments, the recombinant peptide has the ZFP-362 as (i), a VPR as (ii), a TAT as (iii), a NLS as (iv) and a myc-tag sequence as (v) as provided in SEQ ID NO. 9. In embodiments, the recombinant polypeptide has the sequence of SEQ ID NO: 18, or a derivative thereof.

In another aspect, provided herein is a nucleotide sequence encoding any of the recombinant peptides of the present disclosure.

In embodiments, the nucleotide sequence of the present disclosure has a nucleotide sequence encoding a zinc finger domain. In embodiments, the nucleotide sequence of the present disclosure has the sequence of SEQ ID NO. 3 or a derivative thereof. In embodiments, the nucleotide sequence of the present disclosure has a nucleotide sequence encoding the ZFP-362 or a derivative thereof. In embodiments, the ZFP-362 has the sequence of SEQ ID NO. 12, or a derivative thereof.

In embodiments, the nucleotide sequence of the present disclosure has a nucleotide sequence encoding a peptide capable of transcriptional activation. In embodiments, the nucleotide sequence of the present disclosure has a nucleotide sequence encoding a transcriptional activator. In embodiments, the nucleotide sequence of the present disclosure has the sequence of SEQ ID NO.4 or a derivative thereof. In embodiments, the nucleotide sequence has a nucleotide sequence encoding a VPR or a derivative thereof. In embodiments, the VPR has the sequence of SEQ ID NO. 13 or a derivative thereof. In embodiments, instead of VPR or in combination with VPR, one or more of known transcription activators such as p65 transactivating subunit of NF-kappa B, heat-shock factor 1 (HSF) activation domain, the VP64 (tetramer of VP16) activation domain, synergistic activation mediator (SAM) and any derivatives thereof can be encoded by the nucleotide sequence of the disclosures.

In embodiments, the nucleotide sequence of the present disclosure has a nucleotide sequence encoding a cell-penetrating sequence. In embodiments, the nucleotide sequence of the present disclosure has the sequence of SEQ ID NO.5 or a derivative thereof. In embodiments, the nucleotide sequence has a nucleotide sequence encoding a TAT or a derivative thereof. In embodiments, the TAT has the sequence of SEQ ID NO: 14 or a derivative thereof.

In embodiments, the nucleotide sequence of the present disclosure has a nucleotide sequence encoding a nuclear localization sequence. In embodiments, the nucleotide sequence of the present disclosure has the sequence of SEQ ID NO.6 or a derivative thereof. In embodiments, the nucleotide sequence has a nucleotide sequence encoding an NLS. In embodiments, the NLS has the sequence of SEQ ID NO. 15 or a derivative thereof.

In embodiments, the nucleotide sequence of the present disclosure has a nucleotide sequence encoding an additional sequence for protein stabilization and isolation (or purification). In embodiments, the nucleotide sequence of the present disclosure has the sequence of SEQ ID NO.7 or a derivative thereof. In embodiments, the nucleotide sequence has a nucleotide sequence encoding a myc-tag sequence or a maltose binding peptide (MBP). In embodiments, the myc-tag has the sequence of SEQ ID NO. 16 or a derivative thereof. In embodiments, the nucleotide sequence of the present disclosure has nucleic acid sequence(s) encoding an additional peptide sequence for protein stabilization and isolation (or purification); however, the resulting recombinant peptide does not have such an additional peptide sequence as the additional peptide sequence can be removed during an intermediate isolation and/or purification process In embodiments, the nucleotide sequence of the present disclosure has one or more sequences, each of which encodes one of the following components: (i) a zinc finger domain (e.g. ZFP-362), (ii) a peptide capable of transcription activation (e.g. a transcription activator), (iii) a cell-penetrating sequence, (iv) nuclear localization sequence and (v) additional sequence for protein stabilization and isolation (or purification). In embodiments, the number of each sequence encoding one of the foregoing components that is present in a single molecule of the nucleotide sequence, independently, is 0, 1, 2, 3, 4, 5, 6, 7, 8, 9, 10 or more. Also, any nucleic acid in the nucleotide sequence of the disclosures can be a natural or non-natural nucleic acid, e.g. modified nucleic acid.

In embodiments, the nucleotide sequence of the present disclosure has sequences encoding (i) a zinc finger domain (e.g. ZFP-362) and (ii) a peptide capable of transcription activation (e.g. a transcription activator).

In embodiments, the nucleotide sequence of the present disclosure has sequences encoding (i) a zinc finger domain (e.g. ZFP-362), (ii) a peptide capable of transcription activation (e.g. a transcription activator) and (iii) a cell-penetrating sequence.

In embodiments, the nucleotide sequence of the present disclosure has sequences encoding (i) a zinc finger domain (e.g. ZFP-362), (ii) a peptide capable of transcription activation (e.g. a transcription activator) and (iv) nuclear localization sequence.

In embodiments, the nucleotide sequence of the present disclosure has sequences encoding (i) a zinc finger domain (e.g. ZFP-362), (ii) a peptide capable of transcription activation (e.g. a transcription activator) and (v) additional sequence for protein stabilization and isolation (or purification).

In embodiments, the nucleotide sequence of the present disclosure has sequences encoding (i) a zinc finger domain (e.g. ZFP-362), (ii) a peptide capable of transcription activation (e.g. a transcription activator), (iii) a cell-penetrating sequence and (iv) nuclear localization sequence.

In embodiments, the nucleotide sequence of the present disclosure has sequences encoding (i) a zinc finger domain (e.g. ZFP-362), (ii) a peptide capable of transcription activation (e.g. a transcription activator), (iii) a cell-penetrating sequence and (v) additional sequence for protein stabilization and isolation (or purification).

In embodiments, the nucleotide sequence of the present disclosure has sequences encoding (i) a zinc finger domain (e.g. ZFP-362), (ii) a peptide capable of transcription activation (e.g. a transcription activator), (iv) nuclear localization sequence and (v) additional sequence for protein stabilization and isolation (or purification). In some of these embodiments, the nucleotide sequence has sequences encoding the ZFP-362 as (i), a VPR as (ii), a NLS as (iv) and a myc-tag sequence as (v) as provided in SEQ ID NO. 8. In embodiments, the nucleotide sequence encodes a protein having the sequence of SEQ ID NO. 17 or a derivative thereof.

In embodiments, the nucleotide sequence of the present disclosure has sequences encoding (i) a zinc finger domain (e.g. ZFP-362), (ii) a peptide capable of transcription activation, (iii) a cell-penetrating sequence, (iv) nuclear localization sequence and (v) additional sequence for protein stabilization and isolation (or purification). In some of these embodiments, the nucleotide sequence has sequences encoding the ZFP-362 as (i), a VPR as (ii), a TAT as (iii), a NLS as (iv) and a myc-tag sequence as (v) as provided in SEQ ID NO. 9. In embodiments, the nucleotide sequence encodes a protein having the sequence of SEQ ID NO. 18 or a derivative thereof.

In one aspect, provided is a vector such as an expression vector that has any of the nucleotide sequences of the present disclosure, which encode the recombinant peptide of the present disclosure. Therefore, in embodiments the expression vector can be used to produce the recombinant peptide of the disclosures in cells. The expression vector can be transfected into cells (e.g. eukaryotic cells such as mammalian cells or human cell lines or prokaryotic cells such as *Escherichia coli*, in which the recombinant peptide is expressed and the expressed peptide can be isolated and purified using various techniques available in the field.

In embodiments, the expression vector is capable of directing the expression of nucleic acids to which they are operatively linked. The term "operably linked" means that the nucleotide sequence of interest is linked to regulatory sequence(s) in a manner that allows for expression of the nucleotide sequence. The regulatory sequence may include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on various viral sequences as well as those contemplated for eukaryotic target cells or prokaryotic target cells. The "target cells" may refer to the cells where the expression vector is transfected and the nucleotide sequence encoding the recombinant peptide is expressed. In embodiments, the target cells are the cells used for production of the recombinant peptide of the present disclosure for later use. Therefore, in these embodiments the expressed recombinant peptides are isolated from the target cells and administered to a subject later for a therapeutic purpose, e.g. treatment of HIV in the subject. In alternative embodiments, the target cells may refer to the cells that have latent HIV. Therefore, when the expression vector is transfected into such cells, the recombinant peptide expressed from the vector activates the viral transcription in the cells, activating latent HIV in the target cells. Any vectors can be used so long as they are compatible with the desired or intended target cell. The skilled person in the art can use any suitable vectors known and available in the art depending on their system, e.g. the target cell or the process of culturing cell and purifying the recombinant peptides.

In some examples, a vector has one or more transcription and/or translation control elements. Depending on the target/ vector system utilized, any of a number of suitable transcription and translation control elements, including constitutive and inducible promoters, transcription enhancer elements, transcription terminators, etc. can be used in the expression vector.

Non-limiting examples of suitable eukaryotic promoters (i.e., promoters functional in a eukaryotic cell) include those from cytomegalovirus (CMV) immediate early, H1, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I. The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

In embodiments, the expression vector has sequences encoding one or more of the following components: (i) a zinc finger domain (e.g. ZFP-362), (ii) a peptide capable of transcription activation (e.g. a transcription activator), (iii) a cell-penetrating sequence, (iv) nuclear localization sequence and (v) additional sequence for protein stabilization and isolation (or purification). In embodiments, the number of each sequence encoding one of the foregoing components that is present in a single expression vector, independently, is 0, 1, 2, 3, 4, 5, 6, 7, 8, 9, 10 or more.

Figure 2:
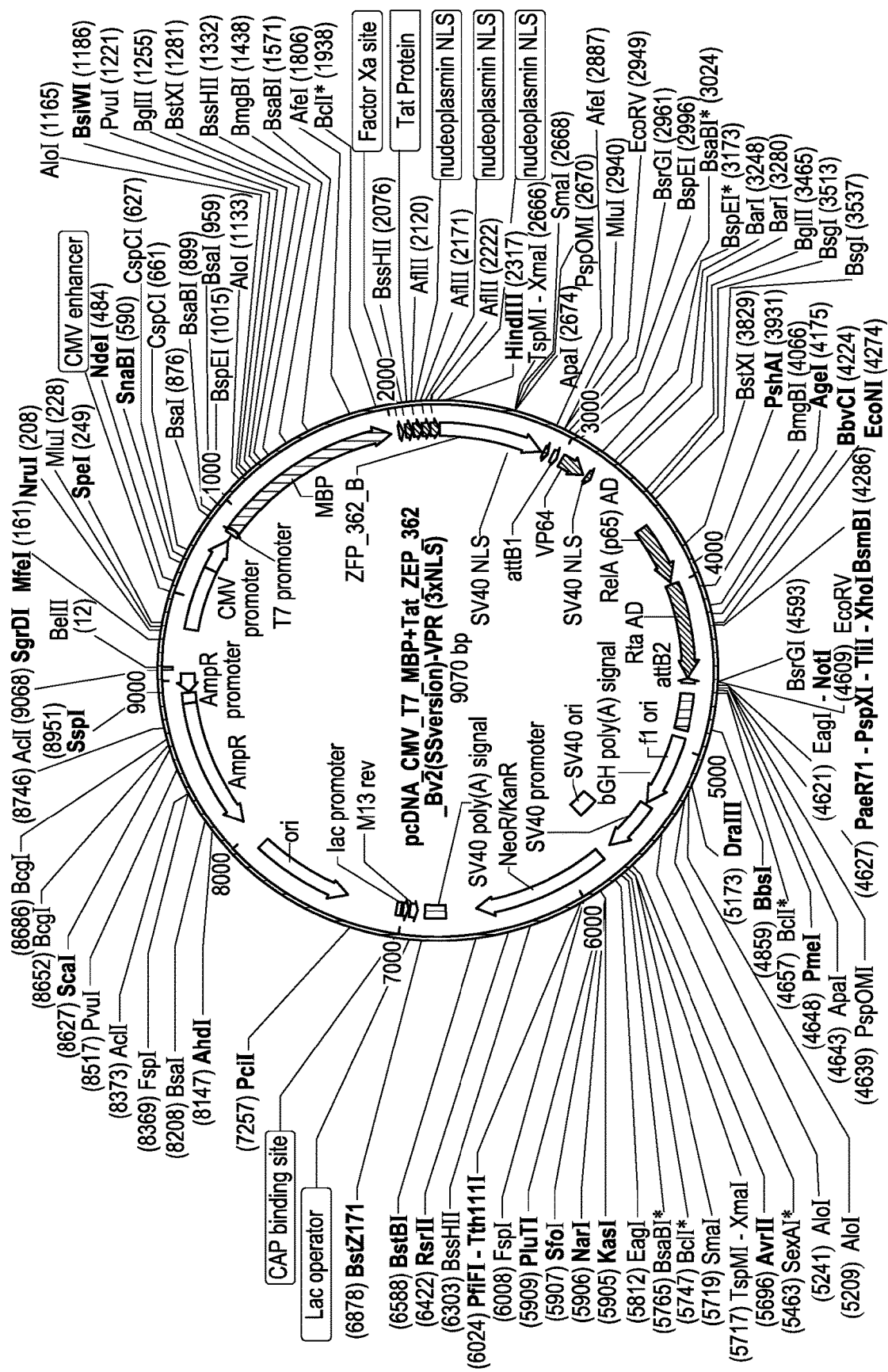
FIG. 2: Vector map of ZFP-362-VPR. The ZFP-362-VPR recombinant protein can be expressed from the CMV promoter and contains a maltose binding protein (MBP) with a factor Xa cleavage site for purification of recombinant protein, the Tat peptide (Tat protein) for nuclear targeting and transit of the recombinant protein through the blood brain barrier, three nucleoplasmin nuclear localization signals (NLS) for enhanced nuclear targeting of the recombinant protein, the ZFP-362 targeted to the NF-kB doublet in the HIV LTR and the VPR transcriptional activator domain (VP64+RelA (p65) and Rta AD). The entire protein is terminated by the bGH poly A signal.

In one example, the expression vector has sequences encoding the ZFP-362 as (i), a VPR as (ii), a TAT as (iii), three NLSs as (iv) and a MBP as (v) as illustrated in FIG. 2. The vector of FIG. 2 has the nucleotide sequence encoding a fusion peptide of the ZFP-362, targeting to the NF-κB doublet in the HIV LTR and the VPR transcriptional activator domain (VP64+RelA (p65) and Rta AD) which is expressed from the CMV promoter. This vector further has a sequence encoding a MBP with a factor Xa cleavage for purification of recombinant peptide, a TAT peptide for nuclear targeting and transit of the recombinant peptide through the blood brain barrier and three nucleoplasmin nuclear localization signals (NLS) for enhanced nuclear targeting of the recombinant peptide. The entire recombinant peptide expressed from this vector is terminated by the bGH poly A signal.

Methods

In one aspect, provided is a method of activating a latent HIV from a cell. The method can have administering any of the recombinant peptides or any of the expression vectors disclosed herein to the cell.

In embodiments, the cell is a cell in which HIV is in the latency. This means that the cell was previously infected with HIV and the HIV or progeny thereof become latent in the cell, e.g. in the episomal or proviral latency. The recombinant peptide of the disclosures may have a zinc finger domain that specifically recognizes and binds to a sequence (i.e. a target sequence) in the HIV LTR. The recombinant peptide may also have a peptide capable of transcription activation such that when the recombinant peptide is bound to the target sequence, it can promote transcription of the HIV LRT sequence, which leads to the transcription of the viral genome. Therefore, when the recombinant peptide is provided into the infected cell with latent HIV, the latent HIV is activated and no longer in its latency due to the activity of the recombinant peptide.

In embodiments, the cell having the viral genome in its own genome (i.e. proviral latency) or as a separate nucleic acid molecule (i.e. episomal latency) is T cell, macrophage, monocyte or microglial cell. Therefore, in embodiments a population of cells having one or more of T cell, macrophage, monocyte and microglial cell that are infected with latent HIV is subjected to the compositions and methods of the present disclosure.

In embodiments, in order to activate latent HIV from the infected cell, the recombinant peptide of the disclosures is provided to the cell. Alternatively, any of the expression vector of the disclosures that encodes the recombinant peptide can be provided to the cell, expressing the recombinant peptide and exhibiting the desired activity, i.e. activation of latent HIV. This provision (or delivery) of the recombinant peptide or the expression vector thereof to the infected cell can be done using various techniques available in the art, which include, but not limited to, alcium phosphate transfection, liposomal transfection, nucleofection, sonoporation, transfection through heat shock, magnetifection and electroporation.

In one aspect, provided is a method of treating HIV in a subject in need thereof. The method may have administering any of the recombinant peptides or any of the expression vectors disclosed herein to the subject.

In embodiments, the subject has one or more cells in which the HIV or progeny thereof is in a latent stage. In embodiments, the latent HIV present in certain cells of the subject is in episomal latency or proviral latency. In embodiments, the infected cells with the latent HIV in the subject can be one or more of T cell, macrophage, monocyte, and microglial cell.

In embodiments, the treatment method of the present disclosure also has selectively killing the infected cells in which the latent HIV is activated by the recombinant peptide.

In embodiments, the method of treating HIV has administering a pharmaceutical composition or formulation to a subject in need of the treatment. In embodiments, the pharmaceutical compositions and formulations for treating HIV, in particular latent HIV in the subject, have compounds in accordance with the present disclosure (e.g. the recombinant peptide, the nucleic acid encoding the recombinant peptide and/or the expression vector expressing the recombinant peptide).

In embodiments, the pharmaceutical composition has one or more compounds of the present disclosure and one or more pharmaceutically acceptable excipients. In embodiments, the pharmaceutical compositions, the compound, or pharmaceutically acceptable salt thereof, is included in a therapeutically effective amount.

The pharmaceutical composition of the present disclosure can be prepared and administered in a wide variety of dosage formulations. Compounds described can be administered orally, rectally, or by injection (e.g. intravenously, intramuscularly, intracutaneously, subcutaneously, intraduodenally, or intraperitoneally). For example, the compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure can additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions can include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, in particular activation of latent HIV from cells present in the subject who was treated with the composition.

In embodiments, the effective amount is an amount sufficient to accomplish a stated purpose (e.g. achieve the effect for which it is administered, treat a disease, reduce the number of cells infected with latent HIV, reduce one or more symptoms of a disease or condition). An example of the effective amount is an amount sufficient to contribute to the desired treatment such as activation of latent HIV from the infected cells that would be sufficient to completely or substantially eradicate the HIV infection from the subject. This amount can also be referred to as a therapeutically effective amount. Thus, in some examples, for the given parameter, an effective amount will show activation of latent HIV from at least 5%, 10%, 15%, 20%, 25%, 40%, 50%, 60%, 75%, 80%, 90%, or at least 100% of the total number of infected cells that are infected with latent HIV. The exact amounts will depend on the purpose of the treatment, and will be ascertainable by one skilled in the art using known techniques.

In embodiments, the effective amount of the composition in accordance with the present disclosure or active ingredient thereof, e.g. the recombinant peptide, the nucleic acid encoding the recombinant peptide and/or the expression vector expressing the recombinant peptide, is administered to a subject in need thereof. In embodiments, the effective amount of the composition or active ingredient thereof to be administered to the subject in one application is about 1 ng/kg of subject body weight, about 10 ng/kg of subject body weight, about 50 ng/kg of subject body weight, about 100 ng/kg of subject body weight, about 500 ng/kg of subject body weight, about 1 µg/kg of subject body weight, about 10 µg/kg of subject body weight, about 50 µg/kg of subject body weight, about 100 µg/kg of subject body weight, about 150 µg/kg of subject body weight, about 200 µg/kg of subject body weight, about 250 µg/kg of subject body weight, about 300 µg/kg of subject body weight, about 350 µg/kg of subject body weight, about 375 µg/kg of subject body weight, about 400 µg/kg of subject body weight, about 450 µg/kg of subject body weight, about 500 µg/kg of subject body weight, about 550 µg/kg of subject body weight, about 600 µg/kg of subject body weight, about 650 µg/kg of subject body weight, about 700 µg/kg of subject body weight, about 750 µg/kg of subject body weight, about 800 µg/kg of subject body weight, about 850 µg/kg of subject body weight, about 900 µg/kg of subject body weight, about 1 mg/kg of subject body weight, about 10 mg/kg of subject body weight, about 50 mg/kg of subject body weight, about 100 mg/kg of subject body weight, about 500 mg/kg of subject body weight, about 1 g/kg of subject body weight or more or any intervening ranges of the of the foregoing. In embodiments, the effective amount of the composition or active ingredient thereof to be administered to the subject in one application is about 0.5 µg, about 1.0 µg, about 1.5 µg, about 2.0 µg, about 2.5 µg, about 3.0 µg, about 3.5 µg, about 4.0 µg, about 4.5 µg about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 1.0 mg, about 1.5 mg, about 2.0 mg, about 2.5 mg, about 3.0 mg, about 3.5 mg, about 4.0 mg, about 4.5 mg about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 1 g or more or any intervening ranges of the foregoing. In embodiments, one or more than one applications of the composition containing the active ingredient can be administered to the subject over a period of time, e.g. several hours, several days, several weeks or several months.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Adjustment and manipulation of established dosages (e.g., frequency and duration) are well within the ability of those skilled in the art.

In embodiments, the compounds described herein can be used as a sole active ingredient(s) of a composition. In embodiments, the compounds can be used in combination with one another, or with other active compounds or drugs known to be useful in treating HIV or with adjunctive agents that may not be effective alone, but may contribute to the efficacy of the active agent. In embodiments, the composition further has one or more other active compounds or drugs known to be useful in treating HIV or cells infected with HIV. In embodiments, the compounds described herein may be co-administered with one another or with one or more other active compounds or drugs known to be useful in treating HIV or cells infected with HIV that are known in the field.

In embodiments, non-limiting examples of the drugs to treat HIV that can be co-administered with the composition of the present disclosure include, but not limited to, efavirenz, emtricitabine, tenofovir disoproxil fumarate rilpivirine, elvitegravir, cobicistat, abacavir, dolutegravir, lamivudine, zidovudine, didanosine, stavudine etravirine, delavirdine mesylate, nevirapine, tipranavir, indinavir, atazanavir, saquinavir, lopinavir, ritonavir, fosamprenavir, darunavir, nelfinavir, simeprevir, boceprevir, ombitasvir, paritaprevir, dasabuvir, enfuvirtide, raltegravir, dolutegravir, elvitegravir, maraviroc or any combinations thereof.

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

Utilizing the teachings provided herein, an effective therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Kits

In one aspect, provided herein is a kit for, in part, activation of latent HIV from infected cells and treatment of HIV. As part of the kit, materials and instruction are provided for both the activation of the latent virus in the infected cells present in a subject, e.g. a patient and the preparation of reaction mixtures for storage and use of kit components.

In embodiments, the kit can contain one or more of the following components:
1. any of the recombinant peptides in the present disclosure,
2. any of the nucleic acid sequences disclosed herein which encodes any of the recombinant peptides,
3. any of the expression vectors disclosed herein which expresses any of the recombinant peptides, and
4. instructions for how to use the kit components.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: 362-ZFP-VPR-TAT Transcriptional Activation of Latent HIV

Figure 3:
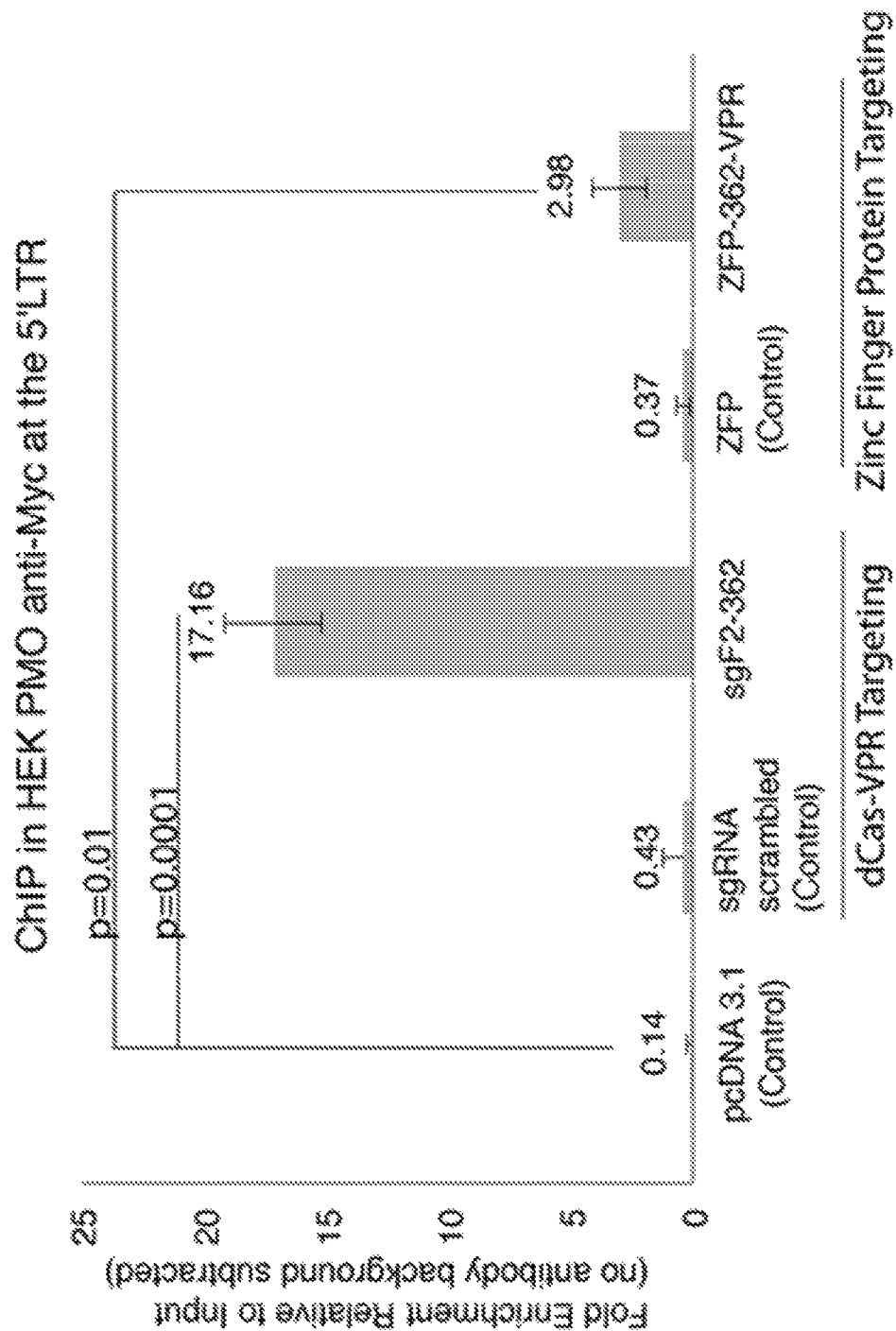
FIG. 3: CHIP analysis of ZFP-362-VPR and dCas-VPR binding to the HIV LTR. HEK PMO cells (containing an integrated HIV vector which expresses GFP) were transfected with either small guide RNA (sg) and dCas-VPR or ZFP-362-VPR and CHIP performed 72 hrs post-transfection to determine binding to the LTR-362 site. The average to triplicate treated cells are shown with the standard deviations and P values from a paired T-test.
Figure 4:
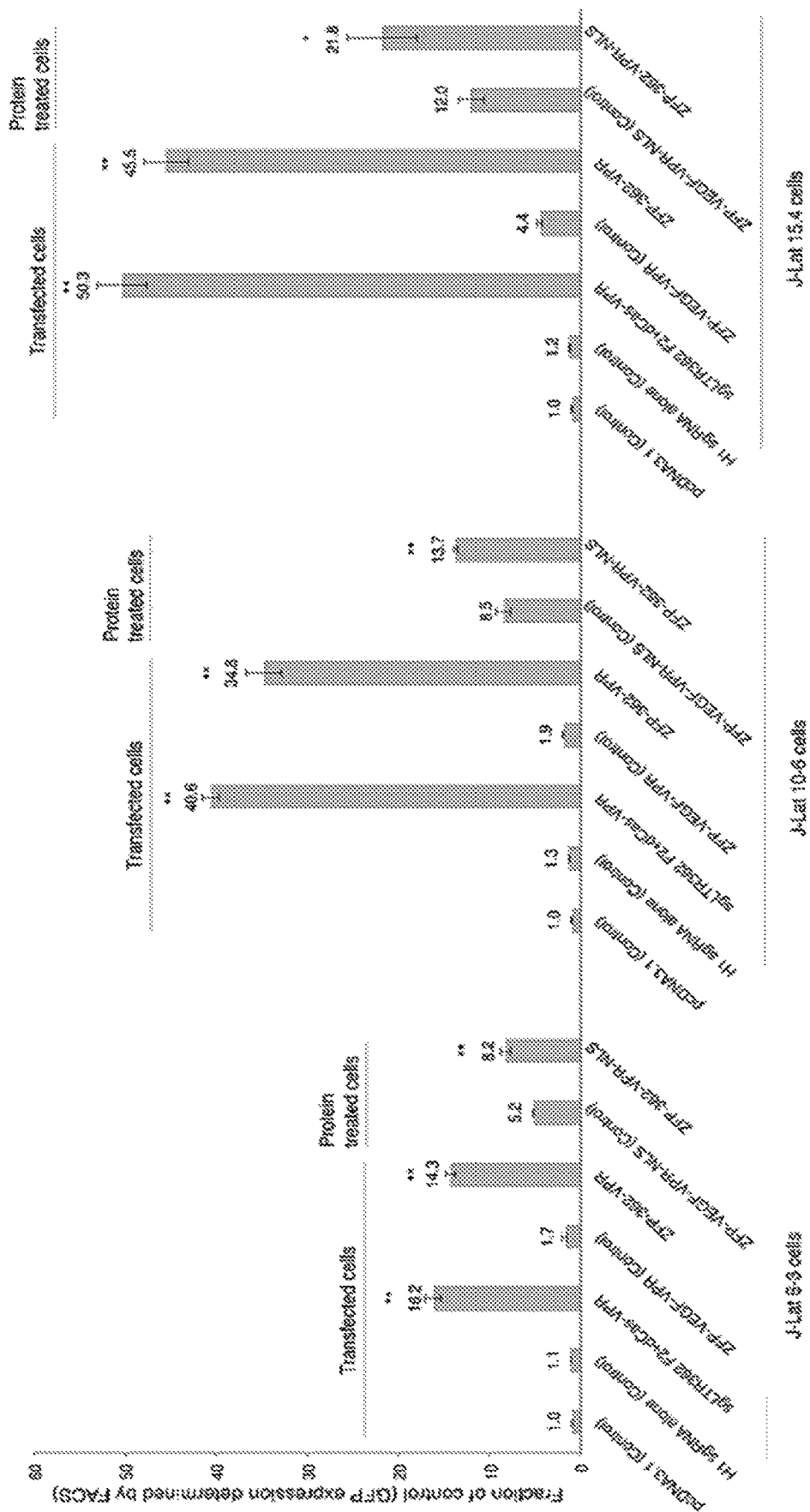
FIG. 4: Effects of Recombinant ZFP-362-VPR expression on J-Lat latent infected cell models. Three different J-Lat cell lines were subjected to either transfection of gRNA F2/dCas-VPR or ZFP-362-VPR and controls or exposed directly to recombinant purified ZFP-362-VPR and controls. The expression of GFP was determined by FACS 72 hrs post-treatment. The results of triplicate treated cultures are shown with the standard deviations. Statistically significant differences, as determined from a paired T-test are also shown (*) P<0.05 and (**) P<0.005.
Figure 5A:
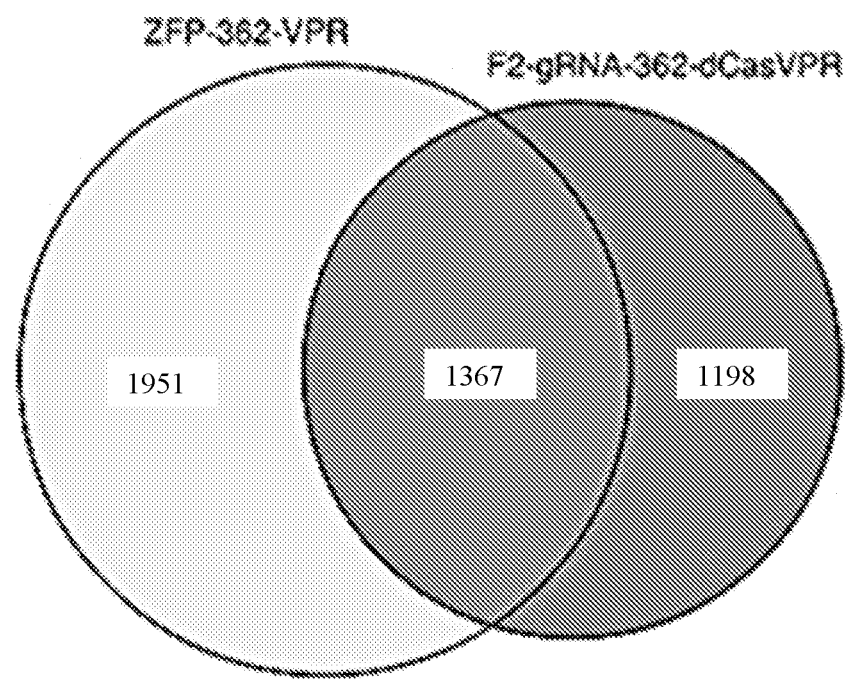
FIGS. 5A-5B: Off-target loci for ZFP-362-VPR vs. gRNA F2-dCas-VPR.
Figure 5B:
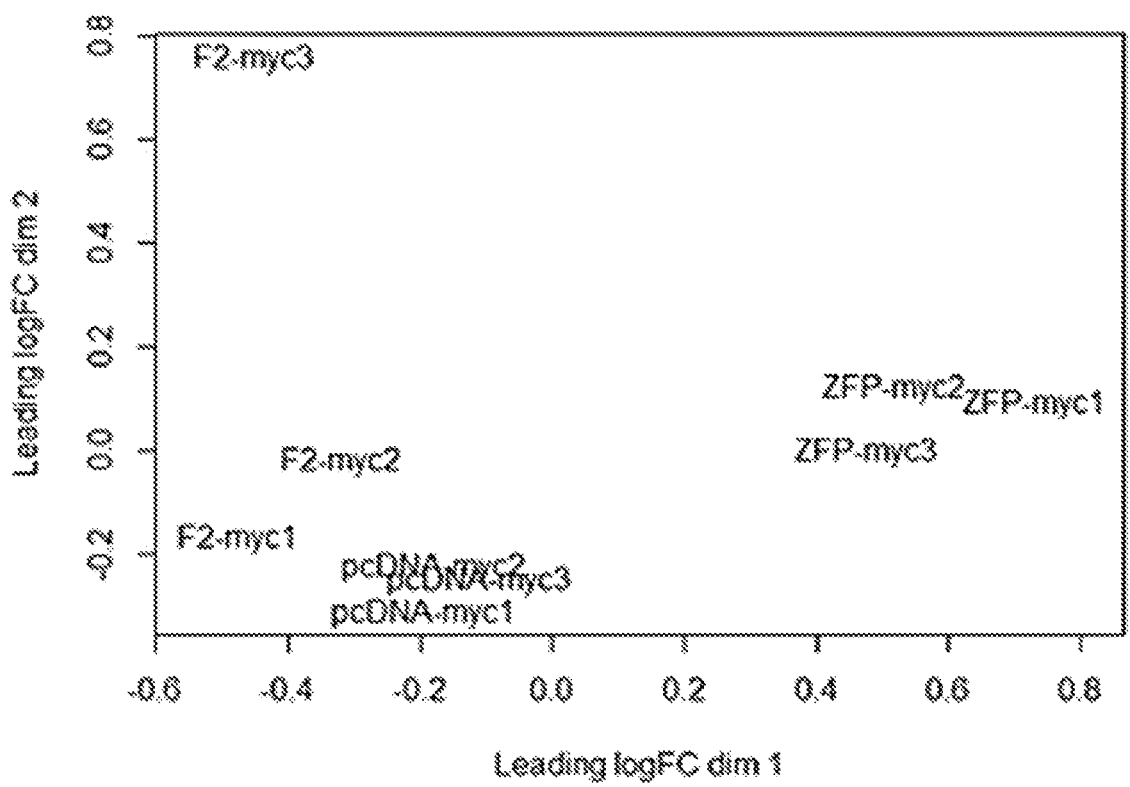

We have developed a therapeutic compound (a unique recombinant protein) that can specifically target and sustainably activate HIV expression from latently infected cells. Using well-established freely available algorithms (ZF Tools Ver 3.0), we developed and screened three zinc finger proteins (ZFPs) and found 1 ZFP, ZFP-362 (FIG. 1A and FIG. 2), that specifically targets the HIV-1 LTR (promoter) and induces activation of HIV transcription at levels comparable to defective CRISPR VPR conjugates (dCas-VPR) (FIGS. 1B-1C), the gold standard in activation of latent HIV. The ZFP-362-VPR targeted activation of HIV LTR expression is specifically targeted to the well-defined NF-κB doublet site, a region known to be susceptible to modulation and control of viral transcription and only found in HIV, as targeting of ZFP-362-VPR to cells lacking this site are not activated (FIG. 1D) compared with those containing this site (FIG. 1C). Moreover, CHIP analysis demonstrated that ZFP-362-VPR binds to the 5' LTR along with defective CRISPR targeting as a control (FIG. 3). Lastly, the recombinant form of ZFP-362-VPR was functional in recombinant protein form when contrasted with control crude-lysates (FIG. 4).

Figure 1B:
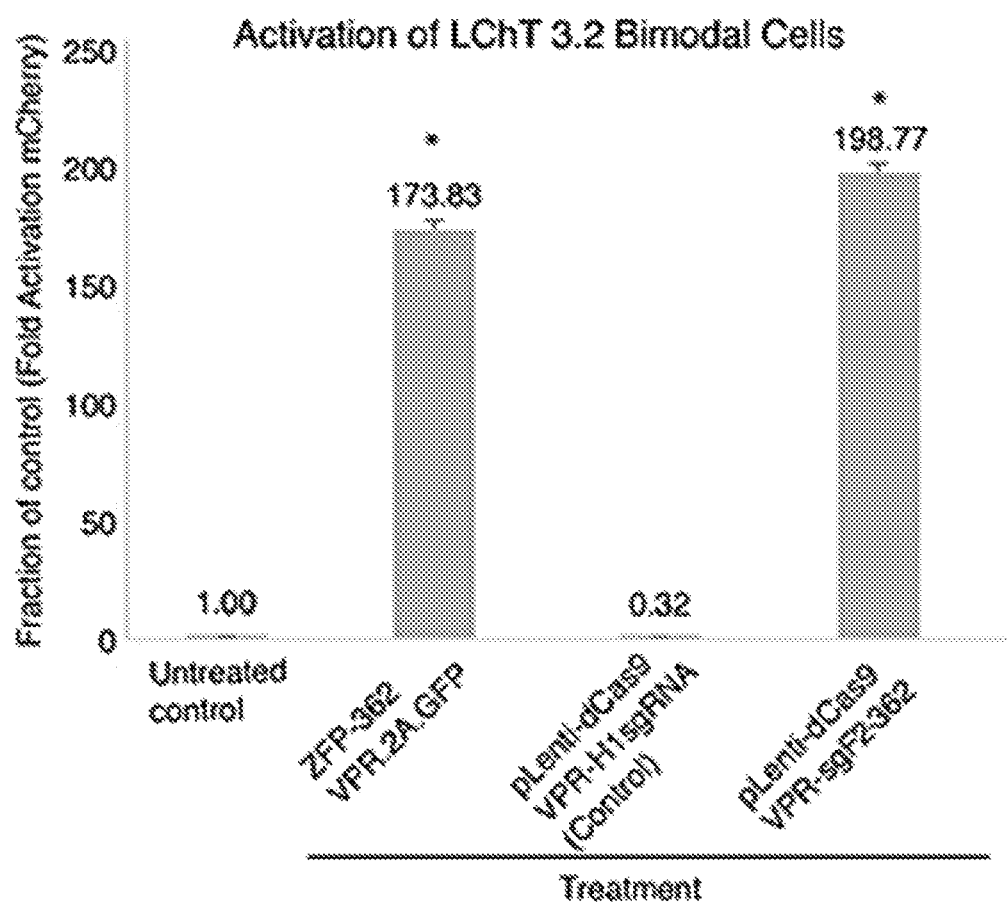
Figure 1C:
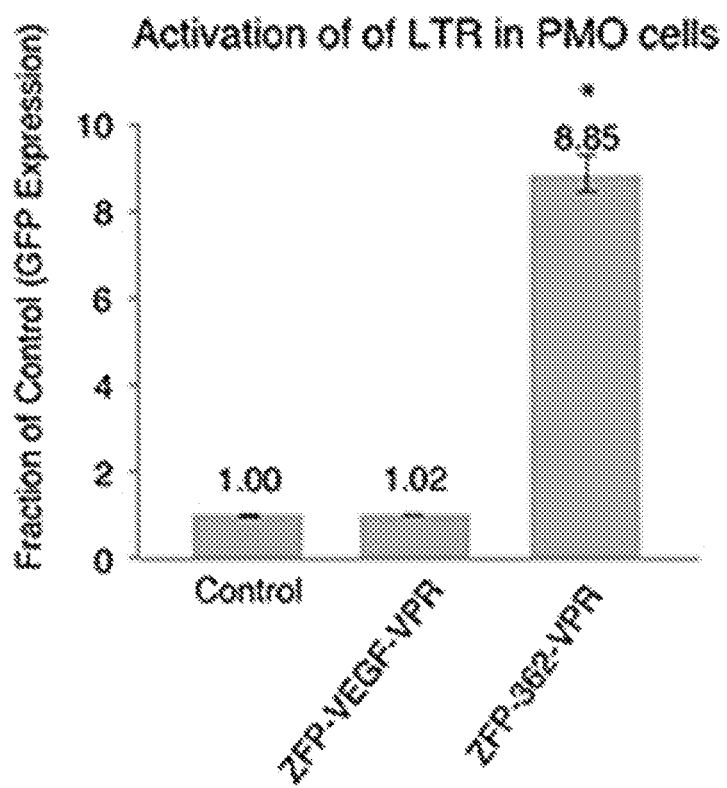
Figure 1D:
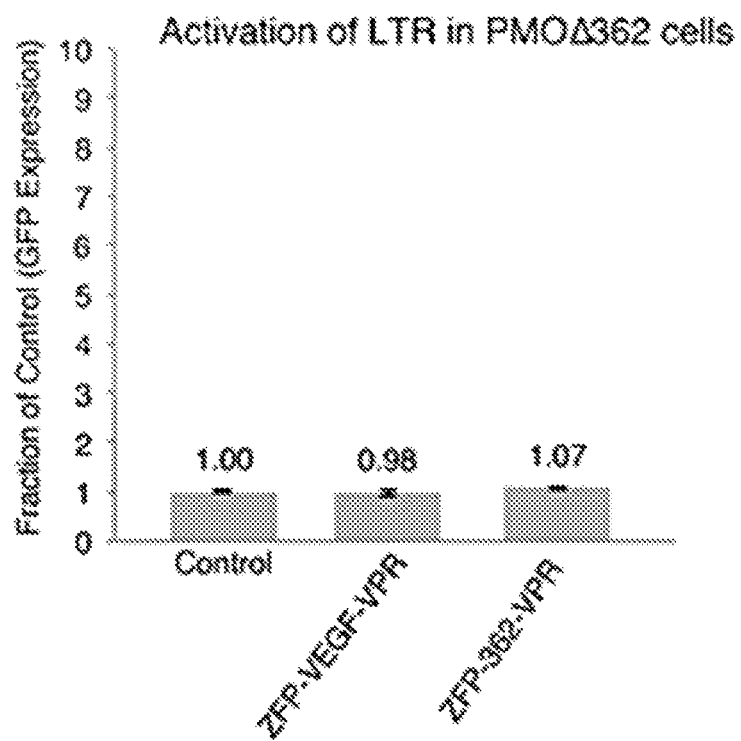

We have developed the Tat peptide conjugate as part of the ZFP-362-VPR described here (FIG. 1A). This recombinant protein ZFP-362-VPR (FIG. 2), which contains the Tat peptide domain as well as various nuclear localization signals (NLS) and a cleavable Maltose binding domain, is functional as a protein administered directly to cells or infected patients. The Tat peptide domain facilitates transfer to the nucleus of cells as well as across the blood brain barrier and the ZFP-362 provides the specificity in targeting the NF-κB doublet that is only found in the HIV LTR. Once the LTR is targeted the VPR induces activation of the latent provirus, resulting in activation of latent reservoirs of HIV.

Example 2: Efficacy of the Recombinant ZFP-362-VPR Peptide

Cell culture. The cell lines were maintained in Dulbecco's modified Eagle medium (DMEM, Thermo Scientific, MA, USA) and 10% fetal bovine serum (FBS). The HEK293-GP160 (92UG037.8) cell line was used and the media was supplemented with 1.5 ug/ml puromycin. The cell lines were cultured at 37° C. with 5% $CO_2$.

Transfection of cells. ZFP-362 and gRNAs with dCas-VPR as well as controls were transfected directly into pMo or LChiT cells (~1 μg of plasmid total/$10^6$ cells) using Lipofectamine Max or Neon Electroporation (Invitrogen, Carlsbad, Calif.). Expression of GFP (pMo-GFP) or mCherry (LChIT CEM cells) was determined using FACS and qRTPCR for GFP or mCherry expression standardized to Beta Actin or GAPDH.

CHIP analysis of ZFP-362-VPR binding the 5' LTR. In order to determine the direct binding of ZFP-362-VPR to the proviral LTR a chromatin immunoprecipitation assay (ChIP) was carried out using Anti-Myc tag antibody (ab9106) with 5' LTR primer 5'-TTTCCGCTGGGGACTTTCCAG-3' (SEQ ID NO:10) and 3' LTR primer 5'-ACT-CAAGGCAAGCTTTATTGAGGC-3'(FIG. 3; SEQ ID NO:11). The no antibody background is subtracted from the sample treatment and controls and input and the treatment and controls are then standardized to the input.

Top 10 off-target promoter loci bound by ZFP-362-VPR (Table 1) and gRNA F2-dCas-VPR (Table 2) were tested. Triplicate treated cells were treated and 72 hrs later CHiP performed with Anti-Myc tag antibody Abcam (ab9132) followed by High throughput deep sequencing. The results below show that the ZFP-362-VPR is very on-target, as good as CRISPR if not better at on targeting.

FIG. 6 shows Table 1: Top ZFP-362-VPR off-target gene promoter bound sites.

FIG. 7 shows Table 2: Top F2-gRNA-362-dCasVPR off-target gene promoter bound sites.

Example 3: Activation of Various HIV-1 Subtypes

Figure 8:
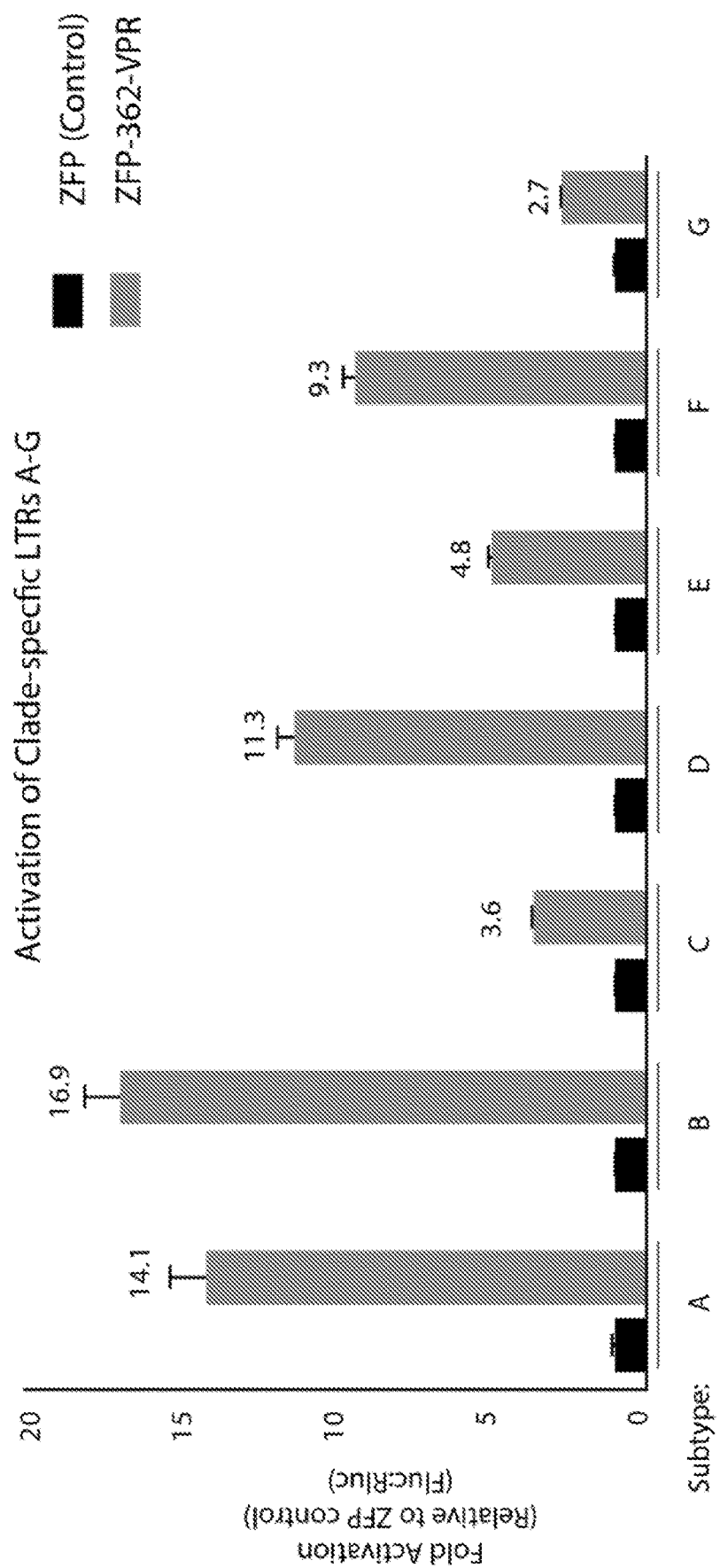
FIG. 8 is a bar graph illustrating activation of clad-specific LTRs in HIV-1 subtypes A, B, C, D, E, F, and G. For subtypes B-E, the averages of triplicate treated cells are shown with standard deviations. In each pair of bars, the first bar of the pair corresponds to results for a ZFP control, and the right bar of the pair corresponds to results for ZFP-362-VPR.

HEK293 cells were transfected in triplicate using Lipofectamine 3000® (Thermo Fisher scientific, Mass., USA) with pcDNA-ZFP-362-VPR or pcDNA-VEGF-VPR, along with vectors expressing firefly luciferase off the LTRs from different subtypes of HIV (Cat. No. 4787, 4788, 4789, 4790, 4791, 4792, 4793; reagents were obtained through the NIH AIDS Reagent Program, Division of AIDS, NIAID, NIH: pBlue3'LTR-luc-A from Dr. Reink Jeeninga and Dr. Ben Berkhout (Jeeninga et al., *J. Virol.* 74:3740-3751, 2000; Klave and Berkhout, *J. Virol.* 68:3830-3840, 1994)). A vector expressing *Renilla* luciferase was included as a background control (pRL-CMV, Promega, Wis., USA). At 48 hrs post-transfection, a Dual-luciferase® Reporter Assay was performed according to manufacturer's instructions and luciferase activity detected on the Glomax® Explorer system (Promega, Wis., USA). The levels of firefly luciferase were normalized to *Renilla* luciferase, and made relative to the pcDNA-VEGF-VPR control. Results are depicted graphically in FIG. 8.

Sequences around the LTR-362 site (SEQ ID NO:1) targeted by ZFP-362 in each of the various subtypes were aligned, and the alignments are illustrated in FIG. 9. Two possible binding sites for subtype C are illustrated. However, of the two sites, SEQ ID NO: 1 is more homologous to the upstream NF-κB III site in subtype C.

REFERENCES

1. Saayman S M, Lazar D C, Scott T A, Hart J R, Takahashi M, Burnett J C, Planelles V, Morris K V, Weinberg M S. Potent and Targeted Activation of Latent HIV-1 Using the CRISPR/dCas9 Activator Complex. Mol. Ther. 2016; 24(3):488-98. doi: 10.1038/mt.2015.202. PubMed PMID: 26581162; PMCID: PMC4786915.
2. Bailus B J, Pyles B, McAlister M M, O'Geen H, Lockwood S H, Adams A N, Nguyen J T, Yu A, Berman R F, Segal D J. Protein Delivery of an Artificial Transcription Factor Restores Widespread Ube3a Expression in an Angelman Syndrome Mouse Brain. Mol. Ther. 2016; 24(3):548-55. doi: 10.1038/mt.2015.236. PubMed PMID: 26727042; PMCID: PMC4786922.

INFORMAL SEQUENCE LISITNG

SEQ ID NO: 1 (The LTR-362 binding site for ZFP-362):
CTTTCCGCTGGGGACTTTCCA

SEQ ID NO: 2 (ZFP-362-binding site in the HIV LTR.):
AATGAAGGAGAGAACAACAGCTTGTTACACCCTATGAGCCAGCATGGGATGGAGGA
CCCGGAGGGAGAAGTATTAGTGTGGAAGTTTGACAGCCTCCTAGCATTTCGTCACAT
GGCCCGAGAGCTGCATCCGGAGTACTACAAAGACTGCTGACATCGAGCTTTCTACA
AGGGACTTTCCGCTGGGGACTTTCCAGGGAGGTGTGGCCTGGGCGGGACTGGGGAG
TGGCGAGCCCTCAGATGCTACATATAAGCAGCTGCTTTTTGCCTGTACTGGGTCTCT
CTGGTTAGACCAGATCTGAGCCTGGGAGCTCTCTGGCTAACTAGGGAACCCACTGCT
TAAG SEQ ID NO: 3 (ZFP-362-VPR-NLS. ZFP-362 sequence)
CTCGAACCTGGGGAGAAACCCTACAAGTGCCCCGAATGCGGGAAAAGCTTCTCACG
CAAGGACAATCTCAAGAATCACCAGCGGACGCACACCGGAGAGAAGCCCTACAAGT
GCCCCGAATGCGGAAAATCATTCTCACAACGCGCCCACTTGGAACGCCACCAGAGA
ACACACACAGGGGAGAAGCCATACAAGTGCCCTGAATGCGGCAAGTCTTTCAGTGA
AAGGTCCCATCTGCGAGAGCACCAGCGAACACATACTGGCGAGAAGCCGTACAAGT
GTCCCGAGTGCGGCAAGAGTTTTAGTTCCAAAAAACACCTGGCCGAACATCAGCGG
ACTCACACAGGGGAGAAGCCCTATAAATGCCCCGAGTGCGGCAAGAGCTTTAGCGA
TCCCGGGGCCCTCGTCCGACATCAGAGGACCCACACAGGGGAGAAACCTTACAAGT
GTCCTGAATGCGGCAAATCTTTCAGCCAGAGAGCAAACCTGCGAGCTCACCAGAGA
ACCCATACTGGCGAAAAGCCTTATAAATGCCCTGAATGCGGGAAGAGTTTCAGCCG
CTCTGACCACCTGACTACTCACCAGCGGACACACACTGGGAAGAAAACTAGCAGCG
CTGCTGACCCCAAGAAGAAGAGGAAGGTG SEQ ID NO: 4 (ZFP-362-VPR-NLS. VPR sequence)
TCGCCAGGGATCCGTCGACTTGACGCGTTGATATCAACAAGTTTGTACAAAAAAGC
AGGCTACAAAGAGGCCAGCGGTTCCGACGGGCTGACGCATTGGACGATTTTGATC
TGGATATGCTGGGAAGTGACGCCCTCGATGATTTTGACCTTGACATGCTTGGTTCGG
ATGCCCTTGATGACTTTGACCTCGACATGCTCGGCAGTGACGCCCTTGATGATTTCG
ACCTGGACATGCTGATTAACTCTAGAAGTTCCGGATCTCCGAAAAAGAAACGCAAA
GTTGGTAGCCAGTACCTGCCCGACACCGACGACCGGCACCGGATCGAGGAAAAGCG
GAAGCGGACCTACGAGACATTCAAGAGCATCATGAAGAAGTCCCCCTTCAGCGGCC
CCACCGACCCTAGACCTCCACCTAGAAGAATCGCCGTGCCCAGCAGATCCAGCGCC
AGCGTGCCAAAACCTGCCCCCAGCCTTACCCCTTCACCAGCAGCCTGAGCACCATC
AACTACGACGAGTTCCCTACCATGGTGTTCCCCAGCGGCCAGATCTCTCAGGCCTCT
GCTCTGGCTCCAGCCCCTCCTCAGGTGCTGCCTCAGGCTCCTGCTCCTGCACCAGCTC
CAGCCATGGTGTCTGCACTGGCTCAGGCACCAGCACCCGTGCCTGTGCTGGCTCCTG
GACCTCCACAGGCTGTGGCTCCACCAGCCCCTAAACCTACACAGGCCGGCGAGGGC
ACACTGTCTGAAGCTCTGCTGCAGCTGCAGTTCGACGACGAGGATCTGGGAGCCCTG
CTGGGAAACAGCACCGATCCTGCCGTGTTCACCGACCTGGCCAGCGTGGACAACAG
CGAGTTCCAGCAGCTGCTGAACCAGGGCATCCCTGTGGCCCCTCACACCACCGAGCC
CATGCTGATGGAATACCCCGAGGCCATCACCCGGCTCGTGACAGGCGCTCAGAGGC
CTCCTGATCCAGCTCCTGCCCCTCTGGGAGCACCAGGCCTGCCTAATGGACTGCTGT
CTGGCGACGAGGACTTCAGCTCTATCGCCGATATGGATTTCTCAGCCTTGCTGGGCT
CTGGCAGCGGCAGCCGGGATTCCAGGGAAGGGATGTTTTTGCCGAAGCCTGAGGCC
GGCTCCGCTATTAGTGACGTGTTTGAGGGCCGCGAGGTGTGCCAGCCAAAACGAAT
CCGGCCATTTCATCCTCCAGGAAGTCCATGGGCCAACCGCCCACTCCCCGCCAGCCT

| INFORMAL SEQUENCE LISITNG |
| --- |
| CGCACCAACACCAACCGGTCCAGTACATGAGCCAGTCGGGTCACTGACCCCGGCAC
CAGTCCCTCAGCCACTGGATCCAGCGCCCGCAGTGACTCCCGAGGCCAGTCACCTGT
TGGAGGATCCCGATGAAGAGACGAGCCAGGCTGTCAAAGCCCTTCGGGAGATGGCC
GATACTGTGATTCCCCAGAAGGAAGAGGCTGCAATCTGTGGCCAAATGGACCTTTCC
CATCCGCCCCAAGGGGCCATCTGGATGAGCTGACAACCACACTTGAGTCCATGAC
CGAGGATCTGAACCTGGACTCACCCCTGACCCCGGAATTGAACGAGATTCTGGATA
CCTTCCTGAACGACGAGTGCCTCTTGCATGCCATGCATATCAGCACAGGACTGTCCA
TCTTCGACACATCTCTGTTT

SEQ ID NO: 5 (ZFP-362-VPR-Tat. TAT sequence)
GGCCGTAAAAAACGTCGTCAGCGCCGTCGCGTCGACCTT SEQ ID NO: 6 (ZFP-362-VPR-NLS. NLS sequence)
AAGCGACCTGCCGCCACAAAGAAGGCTGGACAGGCTAAGAAGAAGAAA SEQ ID NO: 7 (ZFP-362-VPR-NLS. Myc sequence)
GAGCAGAAGCTGATCTCAGAGGAGGACCTGCTT SEQ ID NO: 8 (ZFP-362-VPR-NLS. The recombinant protein is Myc-
NLS-ZFP-362-VPR, is shown below in a 5'-3' manner.):
GAGCAGAAGCTGATCTCAGAGGAGGACCTGCTTAAGCGACCTGCCGCCACAAAGAA
GGCTGGACAGGCTAAGAAGAAGAAACTCGAACCTGGGGAGAAACCCTACAAGTGC
CCCGAATGCGGGAAAAGCTTCTCACGCAAGGACAATCTCAAGAATCACCAGCGGAC
GCACACCGGAGAGAAGCCCTACAAGTGCCCCGAATGCGGAAAATCATTCTCACAAC
GCGCCCACTTGGAACGCCACCAGAGAACACACACAGGGGAGAAGCCCATACAAGTG
CCCTGAATGCGGCAAGTCTTTCAGTGAAAGGTCCCATCTGCGAGAGCACCAGCGAA
CACATACTGGCGAGAAGCCGTACAAGTGTCCCGAGTGCGGCAAGAGTTTTAGTTCC
AAAAAACACCTGGCCGAACATCAGCGGACTCACACAGGGGAGAAGCCCTATAAATG
CCCCGAGTGCGGCAAGAGCTTTAGCGATCCCGGGGCCCTCGTCCGACATCAGAGGA
CCCACACAGGGGAGAAACCTTACAAGTGTCCTGAATGCGGCAAATCTTTCAGCCAG
AGAGCAAACCTGCGAGCTCACCAGAGAACCCATACTGGCGAAAAGCCTTATAAATG
CCCTGAATGCGGGAAGAGTTTCAGCCGCTCTGACCACCTGACTACTCACCAGCGGAC
ACACACTGGGAAGAAAACTAGCAGCGCTGCTGACCCCAAGAAGAAGAGGAAGGTG
TCGCCAGGGATCCGTCGACTTGACGCGTTGATATCAACAAGTTTGTACAAAAAAGC
AGGCTACAAAGAGGCCAGCGGTTCCGGACGGGCTGACGCATTGGACGATTTTGATC
TGGATATGCTGGGAAGTGACGCCCTCGATGATTTTGACCTTGACATGCTTGGTTCGG
ATGCCCTTGATGACTTTGACCTCGACATGCTCGGCAGTGACGCCCTTGATGATTTCG
ACCTGGACATGCTGATTAACTCTAGAAGTTCCGGATCTCCGAAAAAGAAACGCAAA
GTTGGTAGCCAGTACCTGCCCGACACCGACGACCGGCACCGGATCGAGGAAAAGCG
GAAGCGGACCTACGAGACATTCAAGAGCATCATGAAGAAGTCCCCCTTCAGCGGCC
CCACCGACCCTAGACCTCCACCTAGAAGAATCGCCGTGCCCAGCAGATCCAGCGCC
AGCGTGCCAAAACCTGCCCCCAGCCTTACCCCTTCACCAGCAGCCTGAGCACCATC
AACTACGACGAGTTCCCTACCATGGTGTTCCCCAGCGGCCAGATCTCTCAGGCCTCT
GCTCTGGCTCCAGCCCCTCCTCAGGTGCTGCCTCAGGCTCCTGCTCCTGCACCAGCTC
CAGCCATGGTGTCTGCACTGGCTCAGGCACCAGCACCCGTGCCTGTGCTGGCTCCTG
GACCTCCACAGGCTGTGGCTCACCAGCCCCTAAACCTACACAGGCCGGCGAGGGC
ACACTGTCTGAAGCTCTGCTGCAGCTGCAGTTCGACGACGAGGATCTGGGAGCCCTG
CTGGGAAACAGCACCGATCCTGCCGTGTTCACCGACCTGGCCAGCGTGGACAACAG
CGAGTTCCAGCAGCTGCTGAACCAGGGCATCCCTGTGGCCCCTCACACCACCGAGCC
CATGCTGATGGAATACCCCGAGGCCATCACCCGGCTCGTGACAGGCGCTCAGAGGC
CTCCTGATCCAGCTCCTGCCCCTCTGGGAGCACCAGGCCTGCCTAATGGACTGCTGT
CTGGCGACGAGGACTTCAGCTCTATCGCCGATATGGATTTCTCAGCCTTGCTGGGCT
CTGGCAGCGGCAGCCGGGATTCCAGGGAAGGGATGTTTTGCCGAAGCCTGAGGCC
GGCTCCGCTATTAGTGACGTGTTTGAGGGCCGCGAGGTGTGCCAGCCAAAACGAAT
CCGGCCCATTTCATCCTCCAGGAAGTCCATGGGCCAACCGCCCACTCCCCGCCAGCCT
CGCACCAACACCAACCGGTCCAGTACATGAGCCAGTCGGGTCACTGACCCCGGCAC
CAGTCCCTCAGCCACTGGATCCAGCGCCCGCAGTGACTCCCGAGGCCAGTCACCTGT
TGGAGGATCCCGATGAAGAGACGAGCCAGGCTGTCAAAGCCCTTCGGGAGATGGCC
GATACTGTGATTCCCCAGAAGGAAGAGGCTGCAATCTGTGGCCAAATGGACCTTTCC
CATCCGCCCCAAGGGGCCATCTGGATGAGCTGACAACCACACTTGAGTCCATGAC
CGAGGATCTGAACCTGGACTCACCCCTGACCCCGGAATTGAACGAGATTCTGGATA
CCTTCCTGAACGACGAGTGCCTCTTGCATGCCATGCATATCAGCACAGGACTGTCCA
TCTTCGACACATCTCTGTTT SEQ ID NO: 9 (ZFP-362-VPR-Tat. The recombinant protein is TAT-
Myc-NLS-ZFP-362-VPR is shown below in a 5'-3' manner.
GGCCGTAAAAAACGTCGTCAGCGCCGTCGCGTCGACCTTGAGCAGAAGCTGATCTC
AGAGGAGGACCTGCTTAAGCGACCTGCCGCCACAAAGAAGGCTGGACAGGCTAAG
AAGAAGAAACTCGAACCTGGGGAGAAACCCTACAAGTGCCCCGAATGCGGGAAAA
GCTTCTCACGCAAGGACAATCTCAAGAATCACCAGCGGACGCACACCGGAGAGAAG
CCCTACAAGTGCCCCGAATGCGGAAAATCATTCTCACAACGCGCCCACTTGGAACG
CCACCAGAGAACACACACAGGGGAGAAGCCCATACAAGTGCCCTGAATGCGGCAAG
TCTTTCAGTGAAAGGTCCCATCTGCGAGAGCACCAGCGAACACATACTGGCGAGAA
GCCGTACAAGTGTCCCGAGTGCGGCAAGAGTTTTAGTTCCAAAAAACACCTGGCCG
AACATCAGCGGACTCACACAGGGGAGAAGCCCTATAAATGCCCCGAGTGCGGCAAG
AGCTTTAGCGATCCCGGGGCCCTCGTCCGACATCAGAGGACCCACACAGGGGAGAA
ACCTTACAAGTGTCCTGAATGCGGCAAATCTTTCAGCCAGAGAGCAAACCTGCGAG

| INFORMAL SEQUENCE LISITNG |
| --- |
| CTCACCAGAGAACCCATACTGGCGAAAAGCCTTATAAATGCCCTGAATGCGGGAAG |
| AGTTTCAGCCGCTCTGACCACCTGACTACTCACCAGCGGACACACACTGGGAAGAA |
| AACTAGCAGCGCTGCTGACCCCAAGAAGAAGAGGAAGGTGTCGCCAGGGATCCGTC |
| GACTTGACGCGTTGATATCAACAAGTTTGTACAAAAAAGCAGGCTACAAAGAGGCC |
| AGCGGTTCCGGACGGGCTGACGCATTGGACGATTTTGATCTGGATATGCTGGGAAGT |
| GACGCCCTCGATGATTTTGACCTTGACATGCTTGGTTCGGATGCCCTTGATGACTTTG |
| ACCTCGACATGCTCGGCAGTGACGCCCTTGATGATTTCGACCTGGACATGCTGATTA |
| ACTCTAGAAGTTCCGGATCTCCGAAAAAGAAACGCAAAGTTGGTAGCCAGTACCTG |
| CCCGACACCGACGACCGGCACCGGATCGAGGAAAAGCGGAAGCGGACCTACGAGA |
| CATTCAAGAGCATCATGAAGAAGTCCCCCTTCAGCGGCCCCACCGACCCTAGACCTC |
| CACCTAGAAGAATCGCCGTGCCCAGCAGATCCAGCGCCAGCGTGCCAAAACCTGCC |
| CCCCAGCCTTACCCCTTCACCAGCAGCCTGAGCACCATCAACTACGACGAGTTCCCT |
| ACCATGGTGTTCCCCAGCGGCCAGATCTCTCAGGCCTCTGCTCTGGCTCCAGCCCCT |
| CCTCAGGTGCTGCCTCAGGCTCCTGCTCCTGCACCAGCTCCAGCCATGGTGTCTGCA |
| CTGGCTCAGGCACCAGCACCCGTGCCTGTGCTGGCTCCTGGACCTCCACAGGCTGTG |
| GCTCCACCAGCCCCTAAACCTACACAGGCCGGCGAGGGCACACTGTCTGAAGCTCT |
| GCTGCAGCTGCAGTTCGACGACGAGGATCTGGGAGCCCTGCTGGGAAACAGCACCG |
| ATCCTGCCGTGTTCACCGACCTGGCCAGCGTGGACAACAGCGAGTTCCAGCAGCTGC |
| TGAACCAGGGCATCCCTGTGGCCCCTCACACCACCGAGCCCATGCTGATGGAATACC |
| CCGAGGCCATCACCCGGCTCGTGACAGGCGCTCAGAGGCCTCCTGATCCAGCTCCTG |
| CCCCTCTGGGAGCACCAGGCCTGCCTAATGGACTGCTGTCTGGCGACGAGGACTTCA |
| GCTCTATCGCCGATATGGATTTCTCAGCCTTGCTGGGCTCTGGCAGCGGCAGCCGGG |
| ATTCCAGGGAAGGGATGTTTTTGCCGAAGCCTGAGGCCGGCTCCGCTATTAGTGACG |
| TGTTTGAGGGCCGCGAGGTGTGCCAGCCAAAACGAATCCGGCCATTTCATCCTCCAG |
| GAAGTCCATGGGCCAACCGCCCACTCCCCGCCAGCCTCGCACCAACACCAACCGGT |
| CCAGTCCATGAGCCAGTCGGGTCACTGACCCCGGCACCAGTCCCTCAGCCACTGGAT |
| CCAGCGCCCGCAGTGACTCCCGAGGCCAGTCACCTGTTGGAGGATCCCGATGAAGA |
| GACGAGCCAGGCTGTCAAAGCCCTTCGGGAGATGGCCGATACTGTGATTCCCCAGA |
| AGGAAGAGGCTGCAATCTGTGGCCAAATGGACCTTTCCCATCCGCCCCCAAGGGGC |
| CATCTGGATGAGCTGACAACCACACTTGAGTCCATGACCGAGGATCTGAACCTGGA |
| CTCACCCCTGACCCCGGAATTGAACGAGATTCTGGATACCTTCCTGAACGACGAGTG |
| CCTCTTGCATGCCATGCATATCAGCACAGGACTGTCCATCTTCGACACATCTCTGTTT |

SEQ ID NO: 10 (5' LTR primer for CHIP analysis of ZFP-362-VPR
binding the 5' LTR)
TTTCCGCTGGGGACTTTCCAG SEQ ID NO: 11 (3' LTR primer for CHIP analysis of ZFP-362-VPR
binding the 5' LTR)
ACTCAAGGCAAGCTTTATTGAGGC SEQ ID NO: 12 (ZFP-362-VPR-NLS. ZFP-362 sequence)
LEPGEKPYKCPECGKSFSRKDNLKNHQRTHTGEKPYKCPECGKSFSQRAHLERHQRTHT
GEKPYKCPECGKSFSERSHLREHQRTHTGEKPYKCPECGKSFSSKKHLAEHQRTHTGEK
PYKCPECGKSFSDPGALVRHQRTHTGEKPYKCPECGKSFSQRANLRAHQRTHTGEKPY
KCPECGKSFSRSDHLTTHQRTHTGKKTSSAADPKKKRKV SEQ ID NO: 13 (ZFP-362-VPR-NLS. VPR sequence)
SPGIRRLDALISTSLYKKAGYKEASGSGRADALDDFDLDMLGSDALDDFDLDMLGSDA
LDDFDLDMLGSDALDDFDLDMLINSRSSGSPKKKRKVGSQYLPDTDDRHRIEEKRKRTY
ETFKSIMKKSPFSGPTDPRPPPRRIAVPSRSSASVPKPAPQPYPFTSSLSTINYDEFPTMVFP
SGQISQASALAPAPPQVLPQAPAPAPAPAMVSALAQAPAPVPVLAPGPPQAVAPPAPKPT
QAGEGTLSEALLQLQFDDEDLGALLGNSTDPAVFTDLASVDNSEFQQLLNQGIPVAPHT
TEPMLMEYPEAITRLVTGAQRPPDPAPAPLGAPGLPNGLLSGDEDFSSIADMDFSALLGS
GSGSRDSREGMFLPKPEAGSAISDVFEGREVCQPKRIRPFHPPGSPWANRPLPASLAPTPT
GPVHEPVGSLTPAPVPQPLDPAPAVTPEASHLLEDPDEETSQAVKALREMADTVIPQKEE
AAICGQMDLSHPPPRGHLDELTTTLESMTEDLNLDSPLTPELNEILDTFLNDECLLHAMH
ISTGLSIFDTSLF SEQ ID NO: 14 (ZFP-362-VPR-Tat. TAT sequence)
GRKKRRQRRRVDL SEQ ID NO: 15 (ZFP-362-VPR-NLS. NLS sequence)
KRPAATKKAGQAKKKK SEQ ID NO: 16 (ZFP-362-VPR-NLS. Myc sequence)
EQKLISEEDLL SEQ ID NO: 17 (ZFP-362-VPR-NLS. The recombinant protein Myc-NLS-
ZFP-362-VPR, is shown below)
EQKLISEEDLLKRPAATKKAGQAKKKKLEPGEKPYKCPECGKSFSRKDNLKNHQRTHT
GEKPYKCPECGKSFSQRAHLERHQRTHTGEKPYKCPECGKSFSERSHLREHQRTHTGEK
PYKCPECGKSFSSKKHLAEHQRTHTGEKPYKCPECGKSFSDPGALVRHQRTHTGEKPYK
CPECGKSFSQRANLRAHQRTHTGEKPYKCPECGKSFSRSDHLTTHQRTHTGKKTSSAAD
PKKKRKVSPGIRRLDALISTSLYKKAGYKEASGSGRADALDDFDLDMLGSDALDDFDL
DMLGSDALDDFDLDMLGSDALDDFDLDMLINSRSSGSPKKKRKVGSQYLPDTDDRHRI
EEKRKRTYETFKSIMKKSPFSGPTDPRPPPRRIAVPSRSSASVPKPAPQPYPFTSSLSTINY

INFORMAL SEQUENCE LISITNG

```
DEFPTMVFPSGQISQASALAPAPPQVLPQAPAPAPAPAMVSALAQAPAPVPVLAPGPPQA
VAPPAPKPTQAGEGTLSEALLQLQFDDEDLGALLGNSTDPAVFTDLASVDNSEFQQLLN
QGIPVAPHTTEPMLMEYPEAITRLVTGAQRPPDPAPAPLGAPGLPNGLLSGDEDFSSIAD
MDFSALLGSGSGSRDSREGMFLPKPEAGSAISDVFEGREVCQPKRIRPFHPPGSPWANRP
LPASLAPTPTGPVHEPVGSLTPAPVPQPLDPAPAVTPEASHLLEDPDEETSQAVKALREM
ADTVIPQKEEAAICGQMDLSHPPPRGHLDELTTTLESMTEDLNLDSPLTPELNEILDTFLN
DECLLHAMHISTGLSIFDTSLF

SEQ ID NO: 18 (ZFP-362-VPR-Tat. The recombinant protein TAT-Myc-
NLS-ZFP-362-VPR is shown below)
GRKKRRQRRRVDLEQKLISEEDLLKRPAATKKAGQAKKKKLEPGEKPYKCPECGKSFS
RKDNLKNHQRTHTGEKPYKCPECGKSFSQRAHLERHQRTHTGEKPYKCPECGKSFSERS
HLREHQRTHTGEKPYKCPECGKSFSSKKHLAEHQRTHTGEKPYKCPECGKSFSDPGALV
RHQRTHTGEKPYKCPECGKSFSQRANLRAHQRTHTGEKPYKCPECGKSFSRSDHLTTHQ
RTHTGKKTSSAADPKKKRKVSPGIRRLDALISTSLYKKAGYKEASGSGRADALDDFDLD
MLGSDALDDFDLDMLGSDALDDFDLDMLINSRSSGSPKKKRKVGS
QYLPDTDDRHRIEEKRKRTYETFKSIMKKSPFSGPTDPRPPPRRIAVPSRSSASVPKPAPQP
YPFTSSLSTINYDEFPTMVFPSGQISQASALAPAPPQVLPQAPAPAPAPAMVSALAQAPAP
VPVLAPGPPQAVAPPAPKPTQAGEGTLSEALLQLQFDDEDLGALLGNSTDPAVFTDLAS
VDNSEFQQLLNQGIPVAPHTTEPMLMEYPEAITRLVTGAQRPPDPAPAPLGAPGLPNGLL
SGDEDFSSIADMDFSALLGSGSGSRDSREGMFLPKPEAGSAISDVFEGREVCQPKRIRPFH
PPGSPWANRPLPASLAPTPTGPVHEPVGSLTPAPVPQPLDPAPAVTPEASHLLEDPDEETS
QAVKALREMADTVIPQKEEAAICGQMDLSHPPPRGHLDELTTTLESMTEDLNLDSPLTP
ELNEILDTFLNDECLLHAMHISTGLSIFDTSLF
```

What is claimed is:

1. A recombinant peptide comprising a zinc finger domain, wherein said recombinant peptide is encoded by SEQ ID NO. 3 or a derivative thereof having at least 90% nucleic acid sequence identity to SEQ ID NO. 3, and wherein said recombinant peptide binds to a target nucleotide sequence, said target nucleotide sequence comprising the sequence of SEQ ID NO. 1 or a derivative thereof having at least 75% nucleotide sequence identity to the sequence of SEQ ID NO. 1.

2. The recombinant peptide of claim 1, wherein said target nucleotide sequence comprises the sequence of SEQ ID NO. 2 or a derivative thereof having at least 75% nucleotide sequence identity to the sequence of SEQ ID NO. 2.

3. The recombinant peptide of claim 1, wherein said target nucleotide sequence is a long terminal repeat (LTR) sequence of Human Immunodeficiency Virus (HIV).

4. The recombinant peptide of claim 1, wherein the recombinant peptide is encoded by the sequence of SEQ ID NO. 3 or a derivative thereof having at least 95% nucleic acid sequence identity to the sequence of SEQ ID NO. 3.

5. The recombinant peptide of claim 1, wherein the recombinant peptide is encoded by the sequence of SEQ ID NO. 3 or a derivative thereof having at least 99% nucleic acid sequence identity to the sequence of SEQ ID NO. 3.

6. The recombinant peptide of claim 1, wherein the recombinant peptide further comprises a peptide capable of transcriptional activation.

7. The recombinant peptide of claim 6, wherein said peptide capable of transcriptional activation is selected from the group consisting of Viral Protein R (VPR), p65 trans-activating subunit of NF-kappa B, heat-shock factor 1 (HSF) activation domain, VP64 (tetramer of VP16) activation domain and synergistic activation mediator (SAM).

8. The recombinant peptide of claim 1, wherein the recombinant peptide further comprises (a) one or more nuclear localization signal (NLS) sequences, (b) a peptide comprising a TAT peptide, or (c) a peptide comprising a cleavable maltose binding domain.

9. The recombinant peptide of claim 1, wherein the recombinant peptide can cross a blood brain barrier.

10. A nucleotide sequence encoding the recombinant peptide of claim 1, wherein the sequence is SEQ ID NO:3 or a derivative thereof having at least 90% nucleic acid sequence identity to SEQ ID NO. 3.

11. An expression vector comprising the nucleotide sequence of claim 10.

12. The expression vector of claim 11, wherein said nucleotide sequence is expressed under the control of a CMV promoter, a H1 promoter or an EF1 alpha promoter.

* * * * *

UNITED STATES PATENT AND TRADEMARK OFFICE
CERTIFICATE OF CORRECTION

PATENT NO. : 11,618,780 B2
APPLICATION NO. : 16/756632
DATED : April 4, 2023
INVENTOR(S) : Kevin V. Morris et al.

It is certified that error appears in the above-identified patent and that said Letters Patent is hereby corrected as shown below:

In the Specification

In the Statement as to Rights to Inventions Made under Federally Sponsored Research and Development:
Column 1, Line 20 to 22, delete "P01 AI099783-01 and RO1 AI111139-01 awarded by National Institute of Allergy and Infectious Disease (NIH NIAID)." and insert --MH113407, AI099783, AI111139, and DK104681 awarded by the National Institutes of Health.--

Signed and Sealed this
Sixteenth Day of May, 2023

Katherine Kelly Vidal
*Director of the United States Patent and Trademark Office*